United States Patent
Mizumoto et al.

(10) Patent No.: US 9,165,107 B2
(45) Date of Patent: Oct. 20, 2015

(54) URINE ANALYZER AND URINE SAMPLE INFORMATION PROCESSING METHOD

(71) Applicant: Sysmex Corporation, Kobe-shi, Hyogo (JP)

(72) Inventors: Toru Mizumoto, Kobe (JP); Yousuke Tanaka, Kobe (JP); Takayoshi Izumi, Kobe (JP); Keisuke Tsutsumida, Kobe (JP); Yousuke Matsui, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 41 days.

(21) Appl. No.: 13/923,510

(22) Filed: Jun. 21, 2013

(65) Prior Publication Data
US 2013/0282298 A1 Oct. 24, 2013

Related U.S. Application Data

(63) Continuation of application No. PCT/JP2011/078442, filed on Dec. 8, 2011.

(30) Foreign Application Priority Data

Dec. 22, 2010 (JP) .................. 2010-286711
Dec. 22, 2010 (JP) .................. 2010-286712

(51) Int. Cl.
*G06F 19/10* (2011.01)
*G01N 33/493* (2006.01)
*G01N 33/50* (2006.01)

(52) U.S. Cl.
CPC .............. *G06F 19/10* (2013.01); *G01N 33/493* (2013.01); *G01N 33/50* (2013.01)

(58) Field of Classification Search
CPC ......... G06F 19/10; G06F 19/20; G01N 33/50; G01N 33/493; G01N 33/6827; G01N 33/70; G01N 33/80; G01N 33/487; G01N 35/00594; G01N 15/459

USPC ............... 702/22, 23, 25, 26, 30–32; 436/50
See application file for complete search history.

(56) References Cited

U.S. PATENT DOCUMENTS 5,851,487 A * 12/1998 Katayama et al. ........... 422/68.1
2006/0073606 A1 4/2006 Fukuda
(Continued)

FOREIGN PATENT DOCUMENTS

CN 101726614 A 6/2010
CN 101852798 A 10/2010
(Continued)

OTHER PUBLICATIONS

Sekai Hatsu no 'Zenjido Nyo Togo Bunseki Sochi' o Arkray to Kyodo Kaihatsu shi, Global ni Hatsubai, Press Release [online], Sysmex Corp., Oct. 6, 2010, retrieval date Feb. 10, 2012, http://www.sysmex.co.jp/news/press/2010/101006.html, 1 page.
(Continued)

Primary Examiner — Manuel L Barbee
(74) Attorney, Agent, or Firm — Brinks Gilson & Lione

(57) ABSTRACT

A urine analyzer includes a controller configured to perform, when a qualitative measurement result of a sample is obtained and a sediment measurement result of the sample has been stored in a storage section, a cross-check of the obtained qualitative measurement result and the stored sediment measurement result, and to perform, when a sediment measurement result of a sample is obtained and a qualitative measurement result of the sample has been stored in the storage section, a cross-check of the obtained sediment measurement result and the stored qualitative measurement result.

19 Claims, 13 Drawing Sheets

(56) References Cited

U.S. PATENT DOCUMENTS

| | | | |
|---|---|---|---|
| 2007/0072301 A1* | 3/2007 | Fukuda et al. ................. | 436/50 |
| 2010/0248347 A1 | 9/2010 | Tanaka et al. | |

FOREIGN PATENT DOCUMENTS

| | | |
|---|---|---|
| JP | 6-148202 A | 5/1994 |
| JP | 09-218197 A | 8/1997 |
| JP | 2006-098219 A | 4/2006 |
| JP | 2006-098233 A | 4/2006 |
| JP | 2007-322243 A | 12/2007 |
| JP | 2010-107383 A | 5/2010 |
| JP | 2010-190816 A | 9/2010 |
| JP | 2010-236952 A | 10/2010 |
| JP | 2010-237001 A | 10/2010 |

OTHER PUBLICATIONS

Zenjido Nyo Togo Bunseki Sochi UX-2000, Sysmex Corp., © 2011, retrieval date Feb. 10, 2012, http://products.sysmex.co.jp/products/ux-2000/index.html, 2 pages.

International Search Report for International Application No. PCT/JP2011/078442, dated Feb. 28, 2012, 2 pages.

International Preliminary Report on Patentability in corresponding International Application No. PCT/JP2011/078442, and English translation thereof, dated Jun. 25, 2013, 10 pages.

Sysmex Corporation Press Release, "Sysmex aims to expand its market share by the World's First Fully Automated Integrated Urine Analyzer jointly developed with Arkray," obtained from the internet at http://www.sysmex.co.jp/en/news/press/2010/101006.html, Oct. 6, 2010, 2 pages.

* cited by examiner

*FIG. 4A*

QUALITATIVE MEASUREMENT DB

| No. | SAMPLE NUMBER | MEASUREMENT DATE | MEASUREMENT TIME | MEASUREMENT RESULT | | |
|---|---|---|---|---|---|---|
| | | | | GLU | PRO | ... |
| 36 | 0322000087 | 2010/08/10 | 11:00:18 | ... | ... | ... |
| 35 | 0322000086 | 2010/08/10 | 11:00:00 | ... | ... | ... |
| 34 | 0322000093 | 2010/08/10 | 10:50:54 | ... | ... | ... |
| 33 | 0322000092 | 2010/08/10 | 10:50:36 | ... | ... | ... |
| 32 | 0322000091 | 2010/08/10 | 10:50:18 | ... | ... | ... |
| 31 | 0322000090 | 2010/08/10 | 10:50:00 | ... | ... | ... |
| 30 | 0322000089 | 2010/08/10 | 10:32:54 | ... | ... | ... |
| 29 | 0322000088 | 2010/08/10 | 10:32:36 | ... | ... | ... |
| 28 | 0322000087 | 2010/08/10 | 10:32:18 | ... | ... | ... |
| 27 | 0322000086 | 2010/08/10 | 10:32:00 | ... | ... | ... |
| ... | ... | ... | ... | ... | ... | ... |

*FIG. 4B*

SEDIMENT MEASUREMENT DB

| No. | SAMPLE NUMBER | MEASUREMENT DATE | MEASUREMENT TIME | MEASUREMENT RESULT | | |
|---|---|---|---|---|---|---|
| | | | | RBC | WBC | ... |
| 40 | 0322000097 | 2010/08/10 | 13:01:48 | ... | ... | ... |
| 39 | 0322000096 | 2010/08/10 | 13:01:12 | ... | ... | ... |
| 38 | 0322000095 | 2010/08/10 | 13:00:36 | ... | ... | ... |
| 37 | 0322000094 | 2010/08/10 | 13:00:00 | ... | ... | ... |
| 36 | 0322000091 | 2010/08/10 | 10:45:36 | ... | ... | ... |
| 35 | 0322000090 | 2010/08/10 | 10:45:00 | ... | ... | ... |
| 34 | 0322000089 | 2010/08/10 | 10:33:58 | ... | ... | ... |
| 33 | 0322000088 | 2010/08/10 | 10:33:22 | ... | ... | ... |
| 32 | 0322000087 | 2010/08/10 | 10:32:46 | ... | ... | ... |
| 31 | 0322000086 | 2010/08/10 | 10:32:10 | ... | ... | ... |
| ... | ... | ... | ... | ... | ... | ... |

FIG. 5A  MERGED DB

FIG. 5B  CROSS-CHECK TABLE

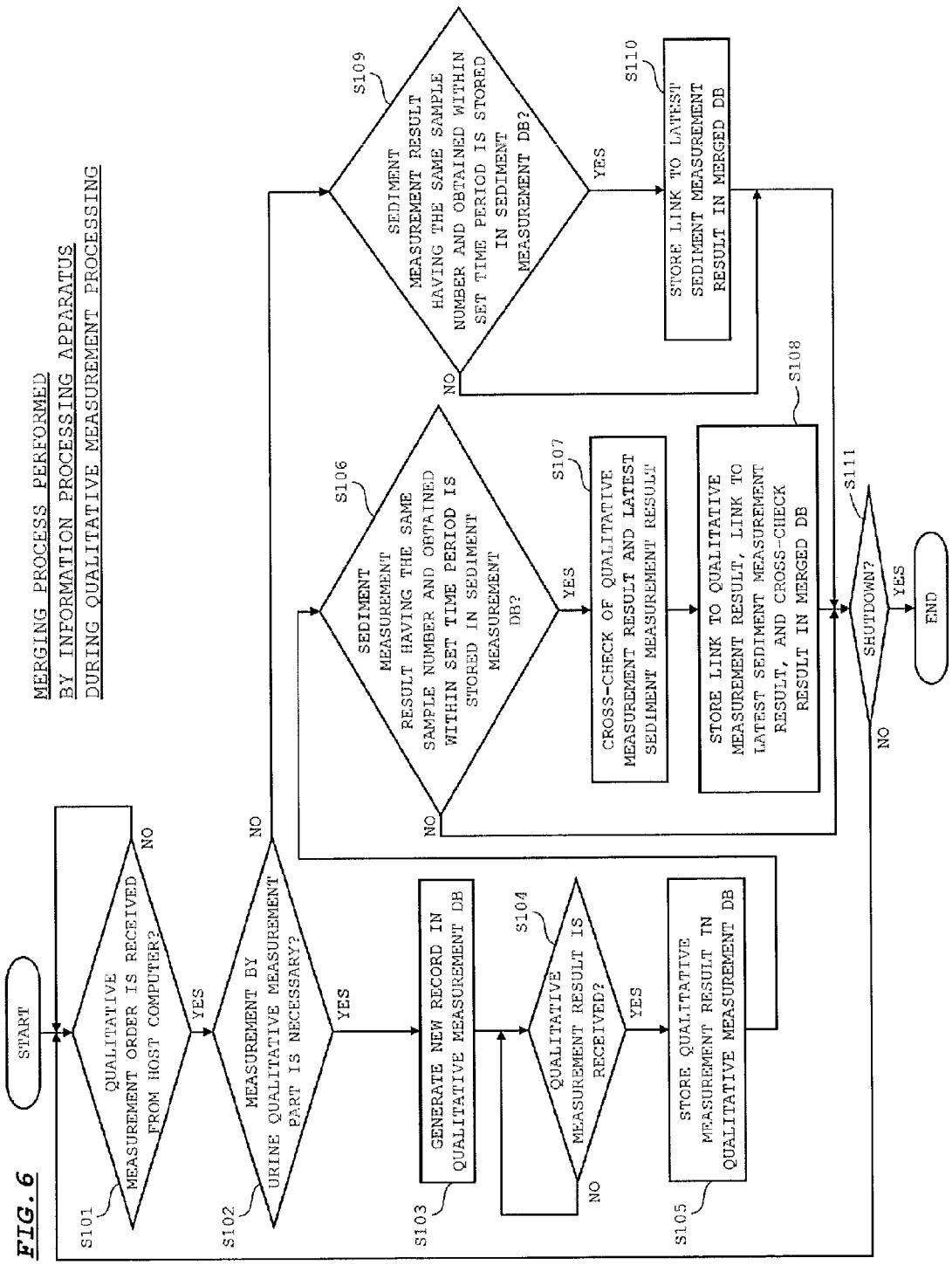

FIG. 12

URINE ANALYZER AND URINE SAMPLE INFORMATION PROCESSING METHOD

RELATED APPLICATIONS

This application is a continuation of PCT/JP2011/078442 filed on Dec. 8, 2011, which claims priority to Japanese Application Nos. 2010-286711 filed on Dec. 22, 2010 and 2010-286712 filed on Dec. 22, 2010. The entire contents of these applications are incorporated herein by reference.

BACKGROUND OF THE INVENTION

1. Field of the Invention

The present invention relates to a urine analyzer which performs urine qualitative measurement and urinary sediment measurement, and a urine sample information processing method.

2. Disclosure of Related Art

Urine analyzers which perform urine qualitative measurement and urinary sediment measurement are known. With respect to such a urine analyzer, there has been proposed a measurement result checking apparatus which performs a cross-check of, among results of urine qualitative measurements and results of urinary sediment measurements, those having a high correlation with each other, and evaluates reliability of the measurement results.

In the above urine analyzer, urine qualitative measurement is performed first, and then urinary sediment measurement is performed. Thus, after a urinary sediment measurement result is obtained, a cross-check is automatically performed. However, in actual test operations, there are cases where urine qualitative measurement is performed after urinary sediment measurement is performed. In this case, a conventional urine analyzer does not automatically perform a cross-check, thus imposing burden on a user.

Further, in urinalysis, there are cases where retesting of urine qualitative measurement or urinary sediment measurement is performed based on a measurement result. When retesting of urine qualitative measurement or urinary sediment measurement is performed, the urine qualitative or urinary sediment measurement result is evaluated singly, and furthermore, it is effective that such a result is evaluated in combination with a measurement result of the other type that was obtained in the past. Further, for evaluation of a current measurement result, it may be effective to compare the current measurement result with a urine qualitative result and a urinary sediment measurement result that were combined together in the past. However, at the time when the current measurement result has been obtained, if a measurement result of the other type to be combined with the current measurement result had become old and deterioration of the sample had advanced, even if the current measurement result is combined with this past measurement result, an appropriate comparison cannot be expected. Furthermore, such a comparison may only result in hindrance of the evaluation.

SUMMARY OF THE INVENTION

A first aspect of the present invention relates to a urine analyzer. The urine analyzer of the present aspect includes: a qualitative measurement part configured to perform measurement for a urine qualitative measurement item; a sediment measurement part configured to perform measurement for a urinary sediment measurement item; a storage section for storing a qualitative measurement result obtained by the qualitative measurement part and a sediment measurement result obtained by the sediment measurement part; and a controller configured to perform, when a qualitative measurement result of a sample is obtained and a sediment measurement result of the sample has been stored in the storage section, a cross-check of the obtained qualitative measurement result and the stored sediment measurement result, and to perform, when a sediment measurement result of a sample is obtained and a qualitative measurement result of the sample has been stored in the storage section, a cross-check of the obtained sediment measurement result and the stored qualitative measurement result.

According to the urine analyzer of the present aspect, irrespective of which of the measurement by the qualitative measurement part or the measurement by the sediment measurement part is performed first, a cross-check can be performed. This can reduce burden on the user, and thus allow smooth comparison and evaluation of measurement results.

A second aspect of the present invention relates to a urine sample information processing method. The urine sample information processing method according to this aspect includes: storing, in a storage section, a qualitative measurement result obtained by measuring a sample for a urine qualitative measurement item; storing, in the storage section, a sediment measurement result obtained by measuring a sample for a urinary sediment measurement item; performing, if a sediment measurement result of a sample has been stored in the storage section at the time when a qualitative measurement result of the sample is obtained, a cross-check of the qualitative measurement result and the sediment measurement result; and performing, if a qualitative measurement result of a sample has been stored in the storage section at the time when a sediment measurement result of the sample is obtained, a cross-check of the sediment measurement result and the qualitative measurement result.

According to the urine sample information processing method of the present aspect, similar effects to those of the first aspect can be obtained.

A third aspect of the present invention relates to a urine analyzer. The urine analyzer according to this aspect includes: a qualitative measurement part configured to perform a measurement for a urine qualitative measurement item; a sediment measurement part configured to perform a measurement for a urinary sediment measurement item; a storage section configured to store a qualitative measurement result obtained by the qualitative measurement part, a sediment measurement result obtained by the sediment measurement part, and combination information indicating a combination of the qualitative measurement result and the sediment measurement result; and a controller. Here, the controller combines a qualitative measurement result newly obtained with a latest sediment measurement result among one or more sediment measurement results of the sample, the one or more sediment measurement results including a sediment measurement result already combined with other qualitative measurement result, and the controller combines a sediment measurement result newly obtained with a latest qualitative measurement result among one or more qualitative measurement results of the sample, the one or more qualitative measurement results including a qualitative measurement result already combined with other sediment measurement result.

With the urine analyzer according to the present aspect, when a plurality of measurements are performed on the same sample, among the qualitative measurement results and the sediment measurement results of the measurements, a history of combinations of latest measurement results is kept. Accordingly, combination of measurement results can be displayed as appropriate. Therefore, with respect to the same sample, the user can compare combinations of a qualitative measurement result and a sediment measurement result with each other, and thus, can more appropriately evaluate the measurement results of the sample.

A forth aspect of the present invention relates to a urine sample information processing method. The urine sample information processing method according to this aspect includes: storing, in a storage section, a qualitative measurement result obtained by measuring a sample for a urine qualitative measurement item; storing, in the storage section, a sediment measurement result obtained by measuring a sample for a urinary sediment measurement item; combining a qualitative measurement result newly obtained with a latest sediment measurement result among one or more sediment measurement results of the sample, the one or more sediment measurement results including a sediment measurement result already combined with other qualitative measurement result; and combining a sediment measurement result newly obtained with a latest qualitative measurement result among one or more qualitative measurement results of the sample, the one or more qualitative measurement results including a qualitative measurement result already combined with other sediment measurement result.

According to the urine sample information processing method of the present aspect, similar effects to those of the third aspect can be obtained.

BRIEF DESCRIPTION OF THE DRAWINGS

The above and other objects and new features of the present invention will be fully clarified by the following description of the embodiment, when read in conjunction with accompanying drawings.

FIGS. 4A and 4B illustrate a concept of a configuration of a qualitative measurement DB and a concept of a configuration of a sediment measurement DB according to an embodiment, respectively;

FIG. 5A illustrates a concept of a configuration of a merged DB and

FIGS. 5B and 5C illustrate a concept of a configuration of a cross-check table according to an embodiment;

FIG. 6 is a flow chart showing a merging process performed by an information processing apparatus during qualitative measurement processing according to an embodiment;

FIG. 12 shows a merged data displaying screen used when displaying merged data including only a qualitative measurement result according to an embodiment.

Figure 1:
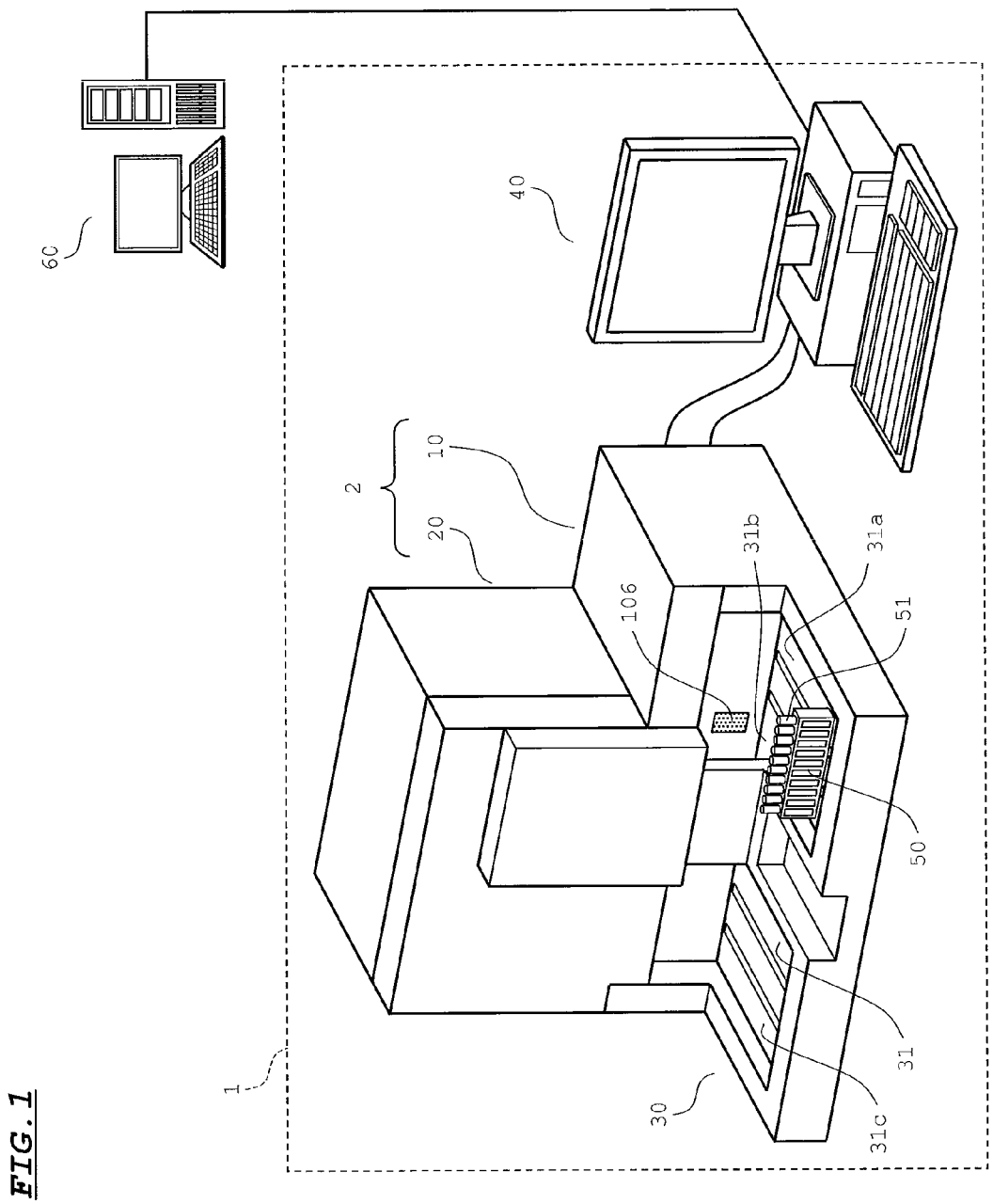
FIG. 1 shows an overall configuration of a system including a urine analyzer according to an embodiment.

It should be noted that the drawings are solely for description and do not limit the scope of the present invention by any degree.

DETAILED DESCRIPTION OF THE PREFERRED EMBODIMENTS

The present embodiment is realized by applying the present invention to a clinical sample analyzer which performs tests (urine qualitative test) regarding urine protein, urine sugar, and the like, and tests (urinary sediment test) regarding red blood cells, white blood cells, epithelial cells, and the like contained in urine. A urinary sediment test is usually performed on a sample for which it has been determined that a urinary sediment test is necessary as a result of a urine qualitative test performed on the sample. However, there are also cases where a urinary sediment test is performed before a urine qualitative test and where only a urinary sediment test is performed. In the present embodiment, a plurality of sample containers respectively containing different samples are set in a rack, the rack is set in a sample analyzer, and testing of the samples are performed.

In the present embodiment, a urine qualitative measurement part 10 corresponds to a "qualitative measurement part" described in claims. A urinary sediment measurement part 20 corresponds to a "sediment measurement part" described in claims. A transport unit 30 corresponds to a "transport part" described in claims. An information processing apparatus 40 corresponds to a "urine sample information processing apparatus" described in claims. A CPU 401 corresponds to a "controller" described in claims. A hard disk 404 corresponds to a "storage section" described in claims. A communication interface 408 corresponds to a "communication section" described in claims. A service setting screen D1 corresponds to a "setting section" described in claims. A result displaying screen D2 corresponds to a "reception screen" described in claims. A merged data displaying screen D3 corresponds to a "measurement result screen" described in claims. A qualitative measurement DB corresponds to a "first database" described in claims. A sediment measurement DB corresponds to a "second database" described in claims. A merged DB corresponds to a "third database" described in claims. However, the correspondence between the claims and the present embodiment is merely an example, and does not limit the claims to the present embodiment.

Hereinafter, a urine analyzer according to the present embodiment will be described with reference to the drawings.

FIG. 1 shows an overall configuration of a system including a urine analyzer 1. The urine analyzer 1 according to the present embodiment includes a measurement unit 2, a transport unit 30, and an information processing apparatus 40.

The measurement unit 2 includes a urine qualitative measurement part 10 which performs urine qualitative tests and a urinary sediment measurement part 20 which performs urinary sediment tests. The urine qualitative measurement part 10 and the urinary sediment measurement part 20 are communicably connected to each other. Moreover, the urine qualitative measurement part 10 and the urinary sediment measurement part 20 are each communicably connected to the information processing apparatus 40. Further, the urine qualitative measurement part 10 is communicably connected to the transport unit 30.

The urine qualitative measurement part 10 is capable of measuring a sample for a plurality of measurement items (urine qualitative measurement items). The urine qualitative measurement items include glucose (GLU), protein (PRO), albumin (ALB), bilirubin (BIL), urobilinogen (URO), pH(PH), occult blood (BLD), ketone body (KET), nitrite (NIT), leukocyte (LEU), creatinine (CRE), and albumin/creatinine ratio (A/C).

The urinary sediment measurement part 20 is capable of measuring a sample for a plurality of measurement items (urinary sediment measurement items). The urinary sediment measurement items include red blood cell (RBC), white blood cell (WBC), epithelial cell (EC), cast (CAST), bacteria (BACT), crystal (X'TAL), yeast-like fungus (YLC), small round cell (SRC), and pathological cast (Path. CAST) including cell components, mucus thread (MUCUS), sperm (SPERM), urine conductivity (Cond.), red blood cell morphology information (RBC-Info.), urine concentration information (Cond.-Info.), and UTI (urinary tract infection) information (UTI-Info.).

The transport unit 30 is a single unit common for the urine qualitative measurement part 10 and the urinary sediment measurement part 20. The transport unit 30 is mounted to the front face of the measurement unit 2 and includes a transport path 31. The transport path 31 has a bottom face of a flat plate shape, provided at a lower level than the upper face of the transport unit 30. In a sample rack 50 which is transported on the transport path 31, ten holders are formed so as to be able to hold ten sample containers 51, respectively. By being held in a holder of the sample rack 50, each sample container 51 is transported on the transport path 31, along with the sample rack 50. A bar code label (not shown) for identifying a sample is affixed to a lateral side of the sample container 51. The information processing apparatus 40 is communicably connected to a host computer 60 via a communication line.

The transport path 31 is composed of a right vessel region 31*a* having a rectangular shape provided on the right side, a left vessel region 31*c* having a rectangular shape provided on the left side, and a connection region 31*b* which is connected to the right vessel region 31*a* and the left vessel region 31*c*. When a user places the sample rack 50 at the front side of the right vessel region 31*a*, this sample rack 50 is transported rearward (in the direction approaching the measurement unit 2), to be located at the rear end of the right vessel region 31*a*. Then, the sample rack 50 is transported leftward in the connection region 31*b*.

A bar code reader 106 reads out bar code information from the bar code label affixed to the sample container 51 located in front of the bar code reader 106. It should be noted that, the bar code reader 106 is controlled by a control section 101 of the urine qualitative measurement part 10 as described later.

The connection region 31*b* is provided with two aspirating positions for aspirating a sample from the sample container 51 held in the sample rack 50. From the sample container 51 located at one of the aspirating positions, the sample is aspirated by means of a nozzle (not shown) provided in the urine qualitative measurement part 10. From the sample container 51 located at the other of the aspirating positions, the sample is aspirated by means of a nozzle (not shown) provided in the urinary sediment measurement part 20. In this manner, aspiration of the sample contained in each sample container 51 on the connection region 31*b* is sequentially performed by the urine qualitative measurement part 10 and the urinary sediment measurement part 20.

When aspiration of all the samples held in the sample rack 50 has been completed, the sample rack 50 is transported leftward along the connection region 31*b* and located at the rear end of the left vessel region 31*c*. The sample rack 50 located at the rear of the left vessel region 31*c* is transported forward, to be sequentially located to the front side of the left vessel region 31*c*. Then, the sample rack 50 located at the front of the left vessel region 31*c* is taken out by the user.

Figure 2:
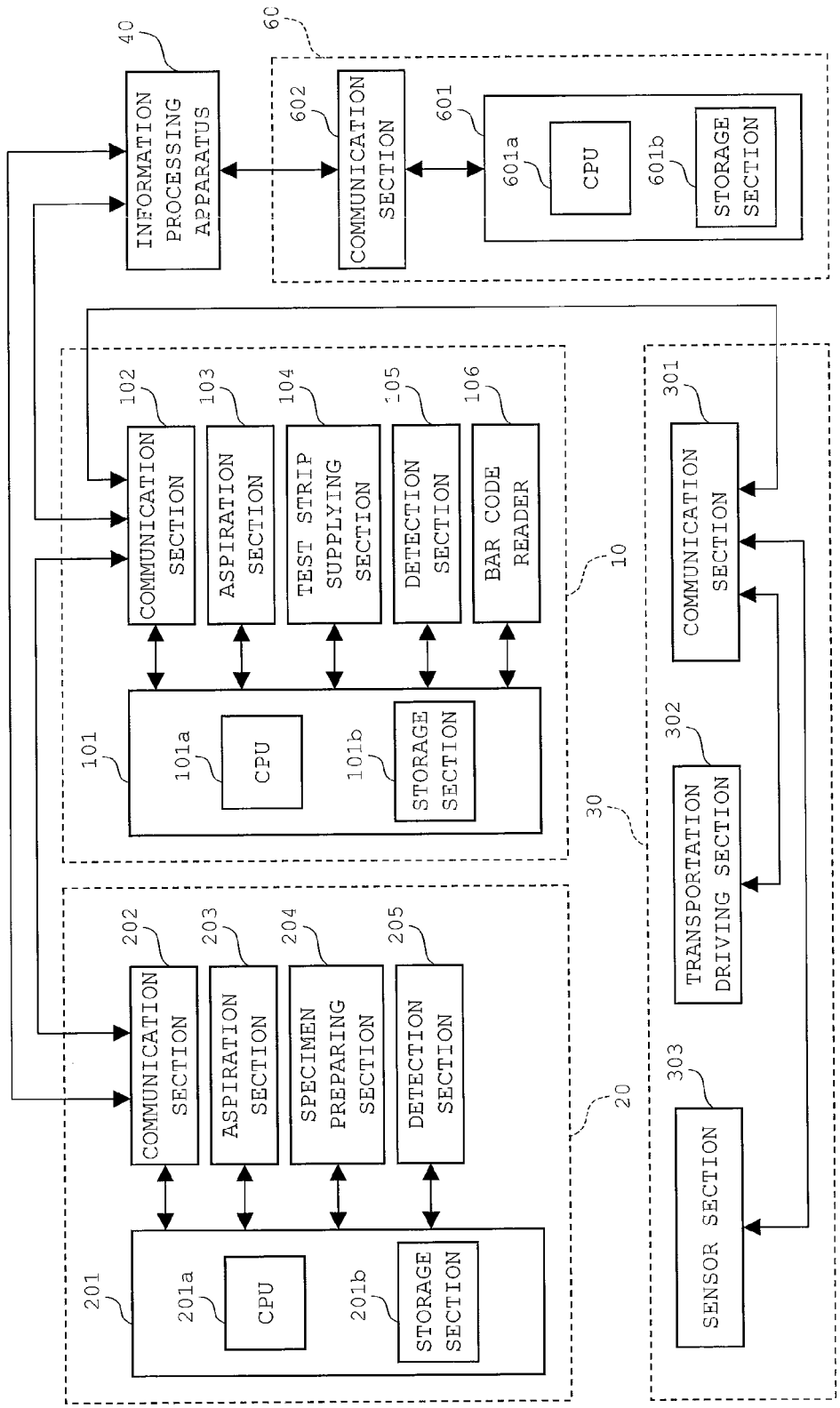
FIG. 2 shows configurations of a urine qualitative measurement part, a urinary sediment measurement part, a transport unit, and a host computer according to an embodiment.

FIG. 2 shows configurations of the urine qualitative measurement part 10, the urinary sediment measurement part 20, the transport unit 30, and the host computer 60.

The urine qualitative measurement part 10 includes the control section 101, a communication section 102, an aspiration section 103, a test strip supplying section 104, a detection section 105, and the bar code reader 106. The control section 101 includes a CPU 101*a* and a storage section 101*b*.

The CPU 101*a* executes computer programs stored in the storage section 101*b* and controls components of the urine qualitative measurement part 10. Further, the CPU 101*a* controls components of the transport unit 30 via the communication section 102. The storage section 101*b* includes storage means such as a ROM, a RAM, and a hard disk.

The communication section 102 processes signals from the control section 101 to output the resultant signals to the urinary sediment measurement part 20, the transport unit 30, and the information processing apparatus 40, and processes signals from the urinary sediment measurement part 20, the transport unit 30, and the information processing apparatus 40 to output the resultant signals to the control section 101. The aspiration section 103 aspirates, via a nozzle provided in the urine qualitative measurement part 10, the sample in the sample container 51 located at one of the aspirating positions described above. The test strip supplying section 104 takes out a test strip necessary for measurement from a test strip feeder in which test strips are stored, and applies as a spot the sample aspirated by the aspiration section 103 onto the taken-out test strip. The detection section 105 measures the test strip on which the sample has been applied as a spot. A measurement result obtained by the measurement is outputted to the control section 101 and analyzed by the CPU 101*a*. The bar code reader 106 reads out bar code information from the bar code label affixed to the sample container 51, and outputs the bar code information to the control section 101.

The urinary sediment measurement part 20 includes a control section 201, a communication section 202, an aspiration section 203, a specimen preparing section 204, and a detection section 205. The control section 201 includes a CPU 201*a* and a storage section 201*b*.

The CPU 201*a* executes computer programs stored in the storage section 201*b* and controls components of the urinary sediment measurement part 20. The storage section 201*b* includes storage means such as a ROM, a RAM, and a hard disk.

The communication section 202 processes signals from the control section 201 to output the resultant signals to the urine qualitative measurement part 10 and the information processing apparatus 40, and processes signals from the urine qualitative measurement part 10 and the information processing apparatus 40 to output the resultant signals to the control section 201. The aspiration section 203 aspirates, via the nozzle provided in the urinary sediment measurement part 20, the sample in the sample container 51 located at one of the supply positions described above. The specimen preparing section 204 mixes and stirs the sample aspirated by the aspiration section 203 and a reagent necessary for measurement, to prepare a specimen for measurement to be performed by the detection section 205. The detection section 205 measures the specimen prepared by the specimen preparing section 204, using a flow cytometer. A measurement result obtained by the measurement is outputted to the control section 201.

The transport unit 30 includes a communication section 301, a transportation driving section 302, and a sensor section 303. The communication section 301 processes signals from the urine qualitative measurement part 10 to output the resultant signals to components of the transport unit 30, and processes signals from components of the transport unit 30 to output the resultant signals to the urine qualitative measurement part 10. The transportation driving section 302 is controlled by the CPU 101a of the urine qualitative measurement part 10. The sensor section 303 includes various types of sensors provided in the transport unit 30, and outputs output signals from these sensors to the urine qualitative measurement part 10 via the communication section 301.

The host computer 60 includes a control section 601 and a communication section 602. The control section 601 includes a CPU 601a and a storage section 601b. The CPU 601a executes computer programs stored in the storage section 601b, and when receiving inquiries about a qualitative measurement order and a sediment measurement order from the information processing apparatus 40, the CPU 601a returns a qualitative measurement order and a sediment measurement order stored in the storage section 601b, respectively. The CPU 601a determines a sediment measurement order for the urinary sediment measurement part 20, based on a measurement result received from the urine qualitative measurement part 10 via the information processing apparatus 40 and criteria stored in the storage section 601b regarding whether measurement is necessary or not. The storage section 601b includes storage means such as a ROM, a RAM, and a hard disk.

Figure 3:
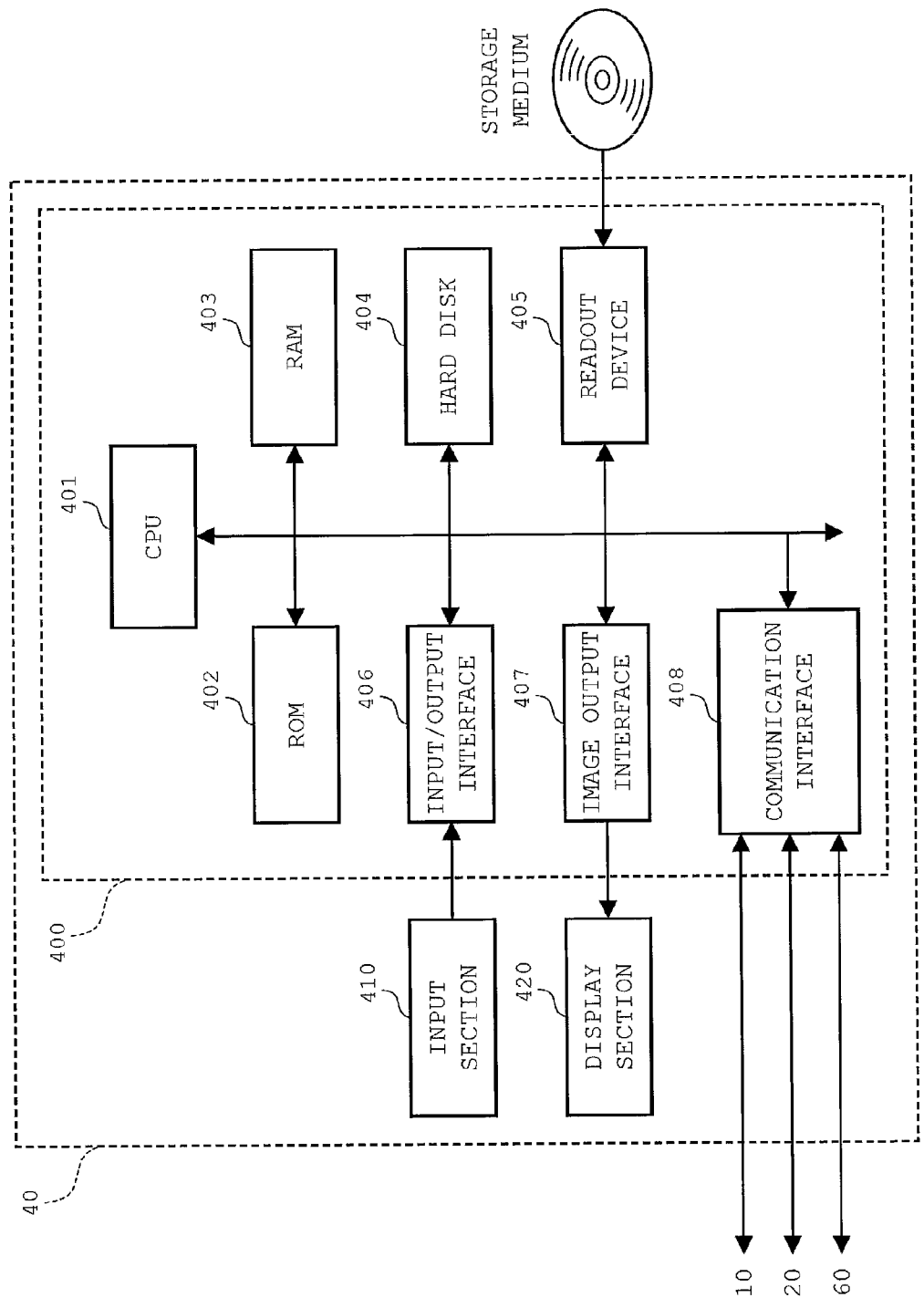
FIG. 3 shows a circuit configuration of an information processing apparatus according to an embodiment.

FIG. 3 shows a circuit configuration of the information processing apparatus 40.

The information processing apparatus 40 is implemented by a personal computer, and includes a body 400, an input section 410, and a display section 420. The body 400 includes a CPU 401, a ROM 402, a RAM 403, a hard disk 404, a readout device 405, an input/output interface 406, an image output interface 407, and a communication interface 408.

The CPU 401 executes computer programs stored in the ROM 402 and computer programs loaded onto the RAM 403. The CPU 401 inquires of the host computer 60 about a qualitative measurement order and a sediment measurement order, based on inquiries about a qualitative measurement order and a sediment measurement order received from the urine qualitative measurement part 10 and the urinary sediment measurement part 20. Further, the CPU 401 transmits the qualitative measurement order and the sediment measurement order received from the host computer 60 to the urine qualitative measurement part 10 and the urinary sediment measurement part 20, respectively.

The RAM 403 is used for reading out computer programs stored in the ROM 402 and the hard disk 404. The RAM 403 is also used as a work area for the CPU 401 when the CPU 401 executes these computer programs.

In the hard disk 404, various computer programs, such as an operating system and application programs, to be executed by the CPU 401, and data used for execution of such computer programs are stored. Moreover, in the hard disk 404, a program for displaying a service setting screen D1 (see FIG. 9B), a result displaying screen D2 (see FIG. 10), and a merged data displaying screen D3 (see FIGS. 11 and 12) is installed.

Moreover, in the hard disk 404, stored are: a qualitative measurement DB (database) (see FIG. 4A) in which results of qualitative measurements (qualitative measurement results) obtained by the urine qualitative measurement part 10 are stored; a sediment measurement DB (see FIG. 4B) in which results of sediment measurements (sediment measurement results) obtained by the urinary sediment measurement part 20 are stored; a merged DB (see FIG. 5A) based on the qualitative measurement results and the sediment measurement results; and a cross-check table (see FIG. 5B).

The readout device 405 is implemented by a CD drive, a DVD drive, or the like, and can read out computer programs and data stored in a storage medium. The input section 410 implemented by a mouse and a keyboard is connected to the input/output interface 406. By the user using the input section 410, data is inputted to the information processing apparatus 40. The image output interface 407 is connected to the display section 420 implemented by a display or the like, and outputs video signals corresponding to image data to the display section 420. The display section 420 displays an image based on the inputted video signals. Further, the communication interface 408 allows data transmission/reception with the urine qualitative measurement part 10, the urinary sediment measurement part 20, and the host computer 60.

FIG. 4A illustrates a concept of a configuration of the qualitative measurement DB.

As shown in FIG. 4A, the qualitative measurement DB includes a number item, a sample number item, a measurement date item, a measurement time item, and a measurement result item for storing a plurality of results of a qualitative measurement. In the number item, a number for uniquely identifying a record (line) is stored. In the sample number item, a sample number assigned to each sample is stored. In the measurement date item and the measurement time item, the date and time at which the measurement by the urine qualitative measurement part 10 was performed are stored. In the measurement result item, a plurality of results of a qualitative measurement performed by the urine qualitative measurement part 10 are stored.

It should be noted that each item in the qualitative measurement DB is stored with some past history thereof retained. That is, the qualitative measurement DB includes a plurality of lines, and information fit within the plurality of lines is not deleted even if new information is inputted.

FIG. 4B illustrates a concept of a configuration of the sediment measurement DB.

As shown in FIG. 4B, the sediment measurement DB includes a number item, a sample number item, a measurement date item, a measurement time item, a measurement result item for storing a plurality of results of a sediment measurement. In the number item, a number for uniquely identifying a record (line) is stored. In the sample number item, a sample number assigned to each sample is stored. In the measurement date item and the measurement time item, the date and time at which the measurement by the urinary sediment measurement part 20 was performed are stored. In the measurement result item, a plurality of results of a sediment measurement performed by the urinary sediment measurement part 20 are stored.

It should be noted that each item in the sediment measurement DB is stored with some past history thereof retained. That is, the sediment measurement DB includes a plurality of lines, and information fit within the plurality of lines is not deleted even if new information is inputted.

FIG. 5A illustrates a concept of a configuration of a merged DB.

As shown in FIG. 5A, the merged DB includes a number item, a qualitative number item, a sediment number item, and a cross-check result item. In the number item, a number for uniquely identifying a record (line) is stored. In the measurement date item and the measurement time item, the date and time at which the record was generated in the merged DB are stored. In the qualitative number item and the sediment number item, the number in the number item of the qualitative measurement DB and the number in the number item of the sediment measurement DB are stored, respectively. It should be noted that, in the case where there is no corresponding number item in the qualitative measurement DB or no corresponding number item in the sediment measurement DB, 0 is stored in the qualitative number item or the sediment number item.

It should be noted that each item in the merged DB is stored with some past history thereof retained. That is, the merged DB includes a plurality of lines, and information fit within the plurality of lines is not deleted even if new information is inputted.

In each record in the merged DB, a combination of the number in the number item of the qualitative measurement DB, stored in the qualitative number item, and the number in the number item of the sediment measurement DB, stored in the sediment number item, serves as "combination information".

In the cross-check result item, a result of a cross-check is stored as appropriate, the cross-check being performed based on a qualitative measurement result obtained from the qualitative measurement DB by using the number in the qualitative number item, and a sediment measurement result obtained from the sediment measurement DB by using the number in the sediment number item. As a result of a cross-check, with respect to any check target (check item) in the cross-check table shown in FIG. 5B, if there is an incompatible relationship (error) between the qualitative measurement result and the sediment measurement result, the number in the number item of the cross-check table corresponding to that check item is stored in the cross-check result item. In the cross-check result item, each record (line) is provided with ten columns for each entering the number, in the number item of the cross-check table, for which an error has been determined. In a column in which no number in the number item of the cross-check table is entered, 0 is stored.

FIG. 5B illustrates a concept of a configuration of the cross-check table.

As shown in FIG. 5B, the cross-check table includes a number item, a target item, and a detail item. In the number item, a number for uniquely identifying a record (line) is stored. In the target item, a combination of a measurement item for the urine qualitative measurement part 10 and a measurement item for the urinary sediment measurement part 20, that is, a qualitative measurement item and a sediment measurement item (check item) targeted by the cross-check, is stored. In the detail item, information is stored that is used for determining whether a measurement result regarding a qualitative measurement item and a measurement result regarding a sediment measurement item targeted by a cross-check are in a predetermined relationship.

Figure 5C:
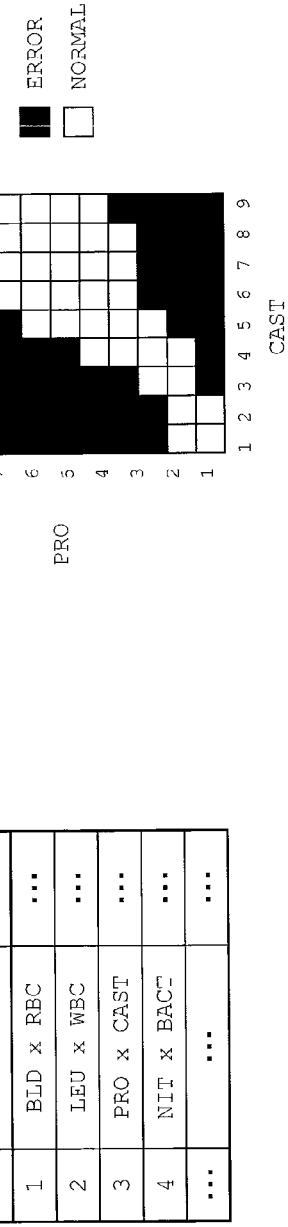

For example, in the detail item of number 3 of the cross-check table, information used for setting a determination criterion shown in FIG. 5C is stored. In FIG. 5C, the horizontal axis represents the level of measurement values of "CAST" in qualitative measurement results, and the vertical axis represents the level of measurement values of "PRO" in sediment measurement results. In this case, when the intersection of the level of a "CAST" measurement value and the level of a "PRO" measurement value is included in the white area (normal), it is determined that the level of the "CAST" measurement value and the level of the "PRO" measurement value are in a compatible relationship (normal), and when the intersection thereof is included in the black area (error), it is determined that the level of the "CAST" measurement value and the level of the "PRO" measurement value are in an incompatible relationship (error). Determinations regarding other check items listed in the cross-check table are performed in the same manner.

When performing a cross-check, with respect to a qualitative measurement result and a sediment measurement result, their values corresponding to the two measurement items shown in each target item in the cross-check table are compared with the determination criterion shown in the corresponding detail item, and it is determined whether or not they are in an incompatible relationship. If they are in an incompatible relationship, the number in the number item of the cross-check table corresponding to that check item is stored in the cross-check result item in the merged DB.

FIG. 6 is a flow chart showing a merging process performed by the information processing apparatus 40 during qualitative measurement processing.

Based on an inquiry about a qualitative measurement order received from the urine qualitative measurement part 10, the CPU 401 of the information processing apparatus 40 transmits an inquiry about the qualitative measurement order to the host computer 60, and then, the CPU 401 causes the processing to wait until receiving an inquiry result (qualitative measurement order) from the host computer 60 (S101). Upon receiving a qualitative measurement order (S101: YES), the CPU 401 transmits the received qualitative measurement order to the urine qualitative measurement part 10, and determines, based on information of whether measurement is necessary included in this qualitative measurement order, whether a measurement by the urine qualitative measurement part 10 is necessary (S102).

When a measurement by the urine qualitative measurement part 10 is necessary (S102: YES), the CPU 401 generates a new record in the qualitative measurement DB (S103). In this new record, a number unique to the record is stored in the number item, the sample number included in the qualitative measurement order is stored in the sample number item, and the other items than these two items remain blank.

Subsequently, the CPU 401 causes the processing to wait until receiving a qualitative measurement result from the urine qualitative measurement part 10 after the measurement by the urine qualitative measurement part 10 has ended (S104). Upon receiving the qualitative measurement result (S104: YES), the CPU 401 stores the received qualitative measurement result in the qualitative measurement DB (S105). That is, in the measurement date and the measurement time of the record generated in S103, the measurement date and time included in the received qualitative measurement result are stored, respectively. Further, in the measurement result item of the record generated in S103, corresponding measurement results included in the received qualitative measurement result are stored.

Subsequently, the CPU 401 determines whether a sediment measurement result that has the same sample number as the sample number included in the received qualitative measurement result and that has been obtained within a set time period before the current time is stored in the sediment measurement DB (S106). It should be noted that the set time period will be described later with reference to FIGS. 9A and 9B. If there is such a sediment measurement result (S106: YES), the processing is advanced to S107, and if there is no such sediment measurement result (S106: NO), the processing is advanced to S111.

When it has been determined as YES in S106, the CPU 401 performs a cross-check using the received qualitative measurement result and the latest sediment measurement result among one or more such sediment measurement results (S107). For determination performed in the cross-check, the cross-check table shown in FIG. 5B is used.

Subsequently, the CPU 401 stores a link to the qualitative measurement result, a link to the latest sediment measurement result, and a cross-check result obtained in S107, in the merged DB (S108). That is, the CPU 401 generates a new record in the merged DB and stores the date and time at which this new record was generated, in the measurement date and the measurement time of this record. Further, in the qualitative number item and the sediment number item of this record, the number in the number item of the qualitative measurement DB representing the qualitative measurement result used in the cross-check, and the number in the number item of the sediment measurement DB representing the sediment measurement result used in the cross-check are stored, respectively. Further, in the cross-check result item of this record, results of the cross-check are stored as appropriate.

Next, when a measurement by the urine qualitative measurement part 10 is not necessary (S102: NO), the CPU 401 determines whether there is a sediment measurement result that has the same sample number as the sample number included in the received qualitative measurement result and that has been obtained within the set time period before the current time is stored in the sediment measurement DB (S109). If there is such a sediment measurement result (S109: YES), the processing is advanced to S110, and if there is no such sediment measurement result (S109: NO), the processing is advanced to S111.

When it has been determined as YES in S109, the CPU 401 stores a link to the latest sediment measurement result among one or more such sediment measurement results, in the merged DB (S110). That is, the CPU 401 generates a new record in the merged DB, and stores the date and time at which this new record was generated, in the measurement date and the measurement time of this record. Further, in the sediment number item of this record, the number in the number item of the sediment measurement DB representing the latest sediment measurement result among one or more such sediment measurement results is stored. Further, in the qualitative number item and the cross-check result item of this record, 0 is stored.

When the user has not performed a shutdown process for the information processing apparatus 40 (S111: NO), the CPU 401 repeats the processes of S101 to S110, and when the user has performed the shutdown process (S111: YES), the CPU 401 ends the processing.

Figure 7:
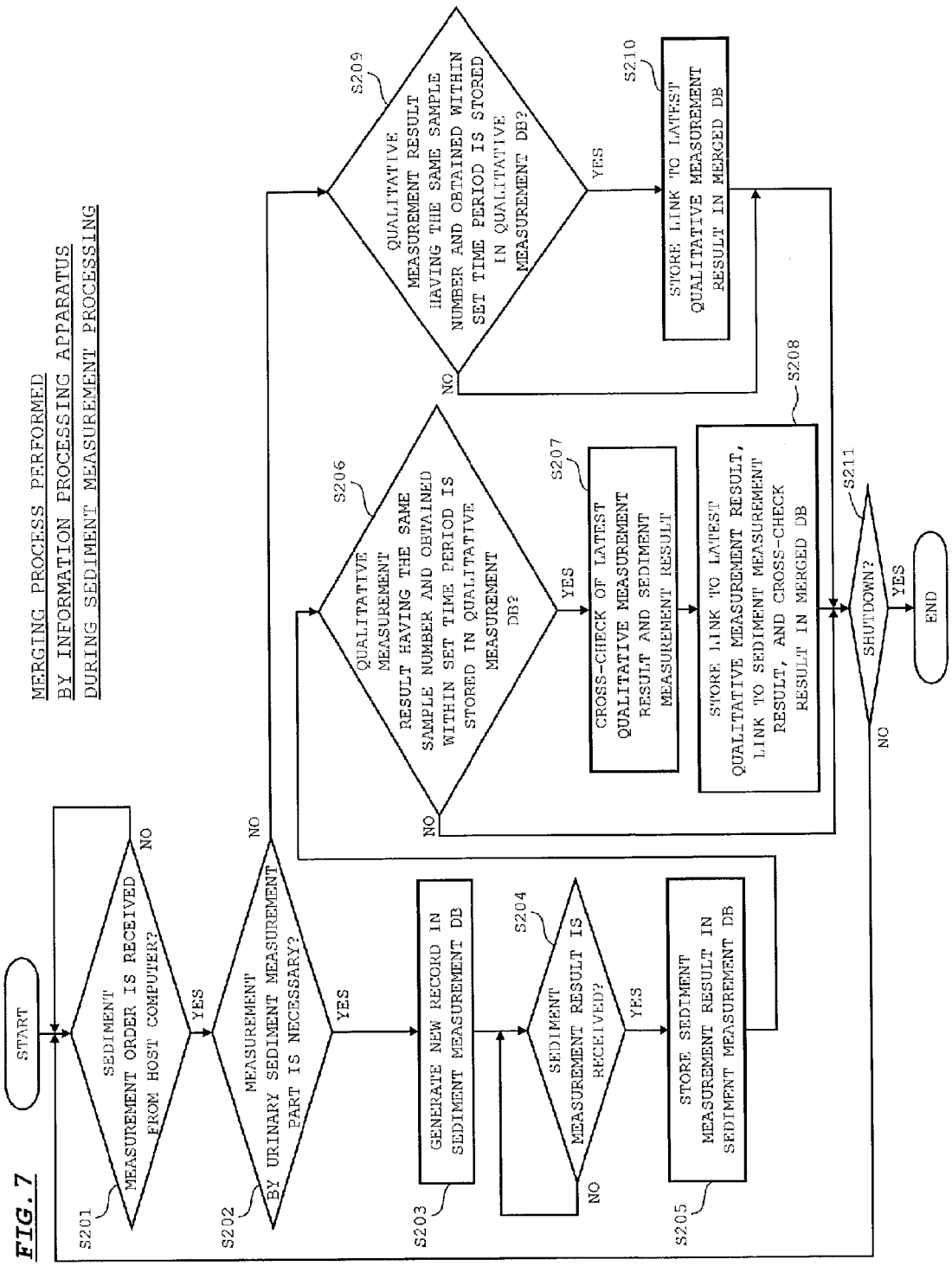
FIG. 7 is a flow chart showing a merging process performed by an information processing apparatus during sediment measurement processing according to an embodiment.

FIG. 7 is a flow chart showing a merging process performed by the information processing apparatus 40 during sediment measurement processing.

Based on an inquiry about a sediment measurement order received from the urinary sediment measurement part 20, the CPU 401 of the information processing apparatus 40 transmits an inquiry about the sediment measurement order to the host computer 60, and then, the CPU 401 causes the processing to wait until receiving an inquiry result (sediment measurement order) from the host computer 60 (S201). Upon receiving a sediment measurement order (S201: YES), the CPU 401 transmits the received sediment measurement order to the urinary sediment measurement part 20, and determines, based on information of whether measurement is necessary included in this sediment measurement order, whether a measurement by the urinary sediment measurement part 20 is necessary (S202).

When a measurement by the urinary sediment measurement part 20 is necessary (S202: YES), the CPU 401 generates a new record in the sediment measurement DB (S203). In this new record, a number unique to the record is stored in the number item, the sample number included in the sediment measurement order is stored in the sample number item, and the other items than these two items remain blank.

Subsequently, the CPU 401 causes the processing to wait until receiving a sediment measurement result from the urinary sediment measurement part 20 after the measurement by the urinary sediment measurement part 20 has ended (S204). Upon receiving the sediment measurement result (S204: YES), the CPU 401 stores the received sediment measurement result in the sediment measurement DB (S205). That is, in the measurement date and the measurement time of the record generated in S203, the measurement date and time included in the received sediment measurement result are stored, respectively. Further, in the measurement result item of the record generated in S203, corresponding measurement results included in the received sediment measurement result are stored.

Subsequently, the CPU 401 determines whether a qualitative measurement result that has the same sample number as the sample number included in the received sediment measurement result and that has been obtained within the set time period before the current time is stored in the qualitative measurement DB (S206). If there is such a qualitative measurement result (S206: YES), the processing is advanced to S207, and if there is no such qualitative measurement result (S206: NO), the processing is advanced to S211.

When it has been determined as YES in S206, the CPU 401 performs a cross-check using the latest qualitative measurement result among one or more such qualitative measurement results and the received sediment measurement result (S207). For determination performed in the cross-check, the cross-check table shown in FIG. 5B is used.

Subsequently, the CPU 401 stores a link to the latest qualitative measurement result, a link to the sediment measurement result, and a cross-check result obtained in S207, in the merged DB (S208). That is, the CPU 401 generates a new record in the merged DB and stores the date and time at which this new record was generated, in the measurement date and the measurement time of this record. Further, in the qualitative number item and the sediment number item of this record, the number in the number item of the qualitative measurement DB representing the qualitative measurement result used in the cross-check, and the number in the number item of the sediment measurement DB representing the sediment measurement result used in the cross-check are stored, respectively. Further, in the cross-check result item of this record, results of the cross-check are stored as appropriate.

Next, when a measurement by the urinary sediment measurement part 20 is not necessary (S202: NO), the CPU 401 determines whether there is a qualitative measurement result that has the same sample number as the sample number included in the received sediment measurement result and that has been obtained within the set time period before the current time is stored in the qualitative measurement DB (S209). If there is such a qualitative measurement result (S209: YES), the processing is advanced to S210, and if there is no such qualitative measurement result (S209: NO), the processing is advanced to S211.

When it has been determined as YES in S209, the CPU 401 stores a link to the latest qualitative measurement result among one or more such qualitative measurement results, in the merged DB (S210). That is, the CPU 401 generates a new record in the merged DB, and stores the date and time at which this new record was generated, in the measurement date and the measurement time of this record. Further, in the qualitative number item of this record, the number in the number item of the qualitative measurement DB representing the latest qualitative measurement result among one or more such qualitative measurement results is stored. Further, in the sediment number item and the cross-check result item of this record, 0 is stored.

When the user has not performed a shutdown process for the information processing apparatus 40 (S211: NO), the CPU 401 repeats the processes of S201 to S210, and when the user has performed the shutdown process (S211: YES), the CPU 401 ends the processing.

Figure 8A:
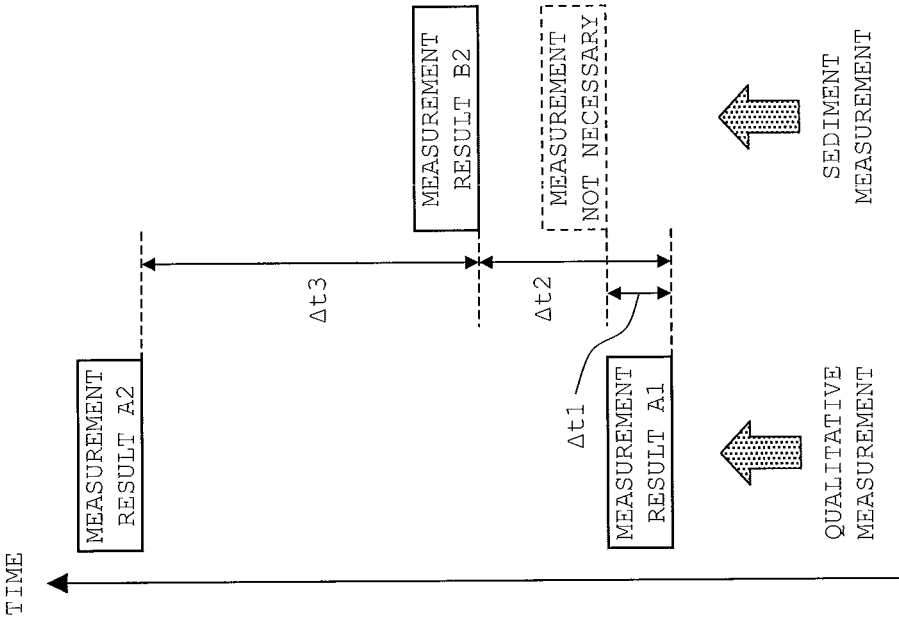
FIGS. 8A and 8B illustrate examples of a merging process according to an embodiment.

FIG. 8A illustrates an example of the merging process.

In FIG. 8A, the vertical axis represents time. FIG. 8A shows that the information processing apparatus 40 received qualitative measurement results A1 and A2 and sediment measurement results B1 and B2, along the time axis. It should be noted that these measurements were all performed onto the same sample, and the dates and times at which the respective measurements were performed and the dates and times at which the information processing apparatus 40 received these measurement results are the same, respectively. It is assumed that: the time difference between the time at which the measurement result A1 was obtained and the time at which the measurement result B1 was obtained is $\Delta t1$; the time difference between the time at which the measurement result A1 was obtained and the time at which the measurement result B2 was obtained is $\Delta t2$; and the time difference between the time at which the measurement result B2 was obtained and the time at which the measurement result A2 was obtained is $\Delta t3$. Moreover, it is assumed that $\Delta t1$ and $\Delta t2$ are each shorter than the set time period mentioned above, and $\Delta t3$ is longer than the set time period.

The measurement result A1 and the measurement result B1 were obtained when a sample container 51 containing the sample and held in a sample rack 50 was transported by the transport unit 30 along the transport path 31 for the first time. The measurement result B2 was obtained when the sample container 51 containing the sample and held in the sample rack 50 was transported by the transport unit 30 along the transport path 31 for the second time. In this case, an order to perform only a urinary sediment measurement on the sample is registered in the host computer 60. The measurement result A2 was obtained when the sample container 51 containing the sample and held in the sample rack 50 was transported by the transport unit 30 along the transport path 31 for the third time. In this case, an order to perform only a urine qualitative measurement on the sample is registered in the host computer 60.

With reference to FIG. 8A, as a result of making an inquiry about a qualitative measurement order with the host computer 60, if it has been determined that a qualitative measurement is necessary, a qualitative measurement is performed on the sample, and the measurement result A1 is obtained. At the time when the measurement result A1 was obtained, since no sediment measurement on the same sample had been performed, no cross-check is performed, and no record is added to the merged DB based on the measurement result A1.

Subsequently, with respect to this sample, an inquiry about a sediment measurement order is made with the host computer 60. When the host computer 60 has determined, based on the measurement result A1, that a sediment measurement is necessary, the host computer 60 transmits an order to perform a sediment measurement on this sample, to the information processing apparatus 40. Accordingly, the sediment measurement is performed and the measurement result B1 is obtained. At the time when the measurement result B1 was obtained, since the measurement result A1 had been obtained by $\Delta t1$ therebefore, a cross-check is performed based on the measurement results A1 and B1, and a record is added to the merged DB.

Subsequently, in order to perform only a sediment measurement again, the user sets, in the host computer 60, a qualitative measurement order and a sediment measurement order such that only a sediment measurement is performed on this sample. Then, the user sets this sample in the right vessel region 31a again, and starts the measurement. Thereafter, as a result of making an inquiry about a qualitative measurement order and a sediment measurement order with the host computer 60, no qualitative measurement is performed on this sample, and only a sediment measurement is performed on this sample, whereby the measurement result B2 is obtained. At the time when the measurement result B2 was obtained, since the measurement result A1 had been obtained by $\Delta t2$ therebefore, a cross-check is performed based on the measurement results A1 and B2, and a record is added to the merged DB. In this manner, the record based on the measurement results A1 and B1 and the record based on the measurement results A1 and B2 are both stored in the merged DB.

Subsequently, in order to perform only a qualitative measurement again, the user sets a qualitative measurement order and a sediment measurement order in the host computer 60. As a result of making an inquiry about a qualitative measurement order with the host computer 60, a qualitative measurement is performed on this sample, and the measurement result A2 is obtained. Then, an inquiry about a sediment measurement order is made with the host computer 60, and a response is made to the effect that no sediment measurement is performed on this sample. Accordingly, a sediment measurement is skipped. At the time when the measurement result A2 was obtained, since the measurement result B2 had been obtained by $\Delta t3$ therebefore, which is longer than the set time period mentioned above, no cross-check is performed based on the measurement results A2 and B2, and no record is added to the merged DB.

Figure 8B:
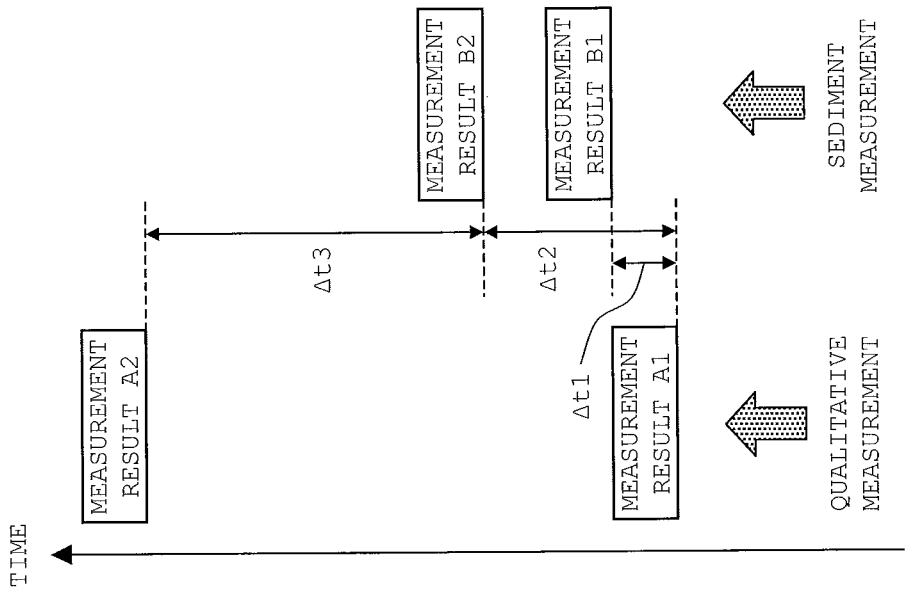

FIG. 8B illustrates a case where, as a result of making an inquiry about a sediment measurement order with the host computer 60 at the timing when the measurement result B1 is obtained as shown in FIG. 8A, it has been determined that a sediment measurement is not necessary.

In this case, at the time when it has been determined that a sediment measurement is not necessary, since the measurement result A1 had been obtained by $\Delta t1$ therebefore, a record is added to the merged DB based only on the measurement result A1. At this time, as shown in FIG. 5A, in the record added to the merged DB, 0 is stored in the sediment number item and all the columns of the cross-check result item.

Figure 9B:
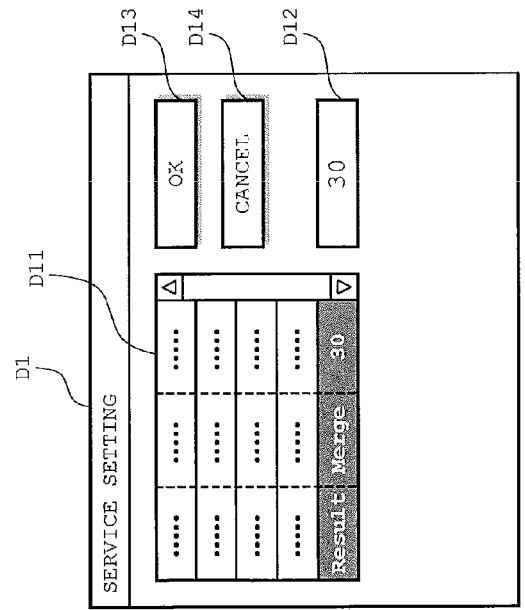
FIG. 9A is a flow chart showing a setting process performed by an information processing apparatus and FIG. 9B shows a service setting screen according to an embodiment.
Figure 9A:
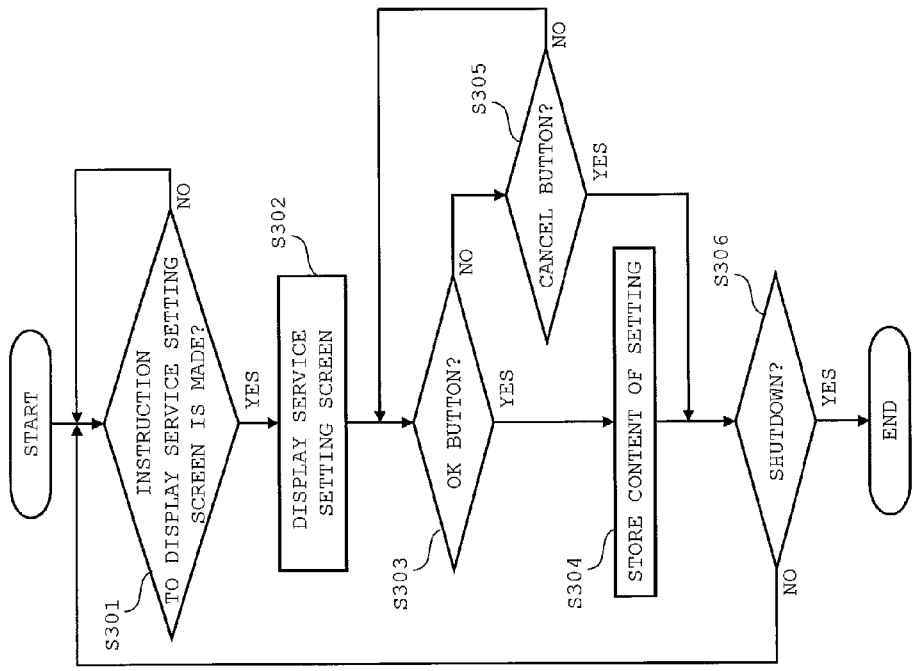

FIG. 9A is a flow chart showing a setting process performed by the information processing apparatus 40.

The CPU 401 of the information processing apparatus 40 determines whether the user has made an instruction to display the service setting screen D1 via the input section 410 (S301). When an instruction to display the service setting screen D1 has been made (S301: YES), the CPU 401 reads, from the hard disk 404, contents of settings of setting items described below, and displays the service setting screen D1 on the display section 420 (S302).

FIG. 9B shows the service setting screen D1. The service setting screen D1 includes a setting item displaying region D11, an input region D12, an OK button D13, and a cancel button D14.

In the setting item displaying region D11, a plurality of changeable setting items regarding the information processing apparatus 40 are displayed. The setting items displayed in the setting item displaying region D11 include the set time period used in S106 in FIG. 6 and S206 in FIG. 7. When the user clicks a setting item in the setting item displaying region D11, the clicked item is displayed in a reversed manner as shown in FIG. 9B, and the content of the setting of this setting item is displayed in the input region D12. The setting item displayed in the reversed manner in FIG. 9B is an item regarding the set time period used in S106 in FIG. 6 and S206 in FIG. 7. The user can change the content of the setting item by rewriting the content displayed in the input region D12 and clicking the OK button D13.

Here, the default value (the value in the initial state) of the set time period in the present embodiment is set to be 30 (minutes). The default value of the set time period is preferably set to be a value that allows a cross-check to be performed even when a reagent or a test strip is replaced between a measurement performed by the urine qualitative measurement part 10 and a measurement performed by the urinary sediment measurement part 20. That is, the default value is preferably set to be longer than or equal to a time period (e.g., 15 minutes) that is assumed to be necessary for a reagent or a test strip to be replaced. Moreover, the default value of the set time period is preferably set to be a value that can maintain the accuracy of a measurement result. A result of a measurement of a sample deteriorated due to lapse of time is considered to have a low accuracy, and thus, in order to prevent a cross-check from being performed based on such a measurement result, the default value of the set time period is preferably set to be shorter than or equal to a time period (e.g., 60 minutes) that is considered to be able to maintain the accuracy of a measurement result.

It should be noted that, when the set time period is set to be 0, it is always determined as NO in S106 in FIG. 6 and S206 and FIG. 7, and thus, a cross-check is prevented from being performed.

With reference back to FIG. 9A, when the service setting screen D1 is displayed (S302), the CPU 401 of the information processing apparatus 40 causes the processing to wait until the OK button D13 or the cancel button D14 is clicked. When the OK button D13 has been clicked (S303: YES), the CPU 401 stores the content of the setting rewritten by the user in the hard disk 404 (S304). When the cancel button D14 has been clicked, (S303: NO, S305: YES), the processing is advanced to S306.

When the user has not performed a shutdown process for the information processing apparatus 40 (S306: NO), the CPU 401 repeats the processes of S301 to S305, and when the user has performed the shutdown process (S306: YES), the processing ends.

Figure 10:
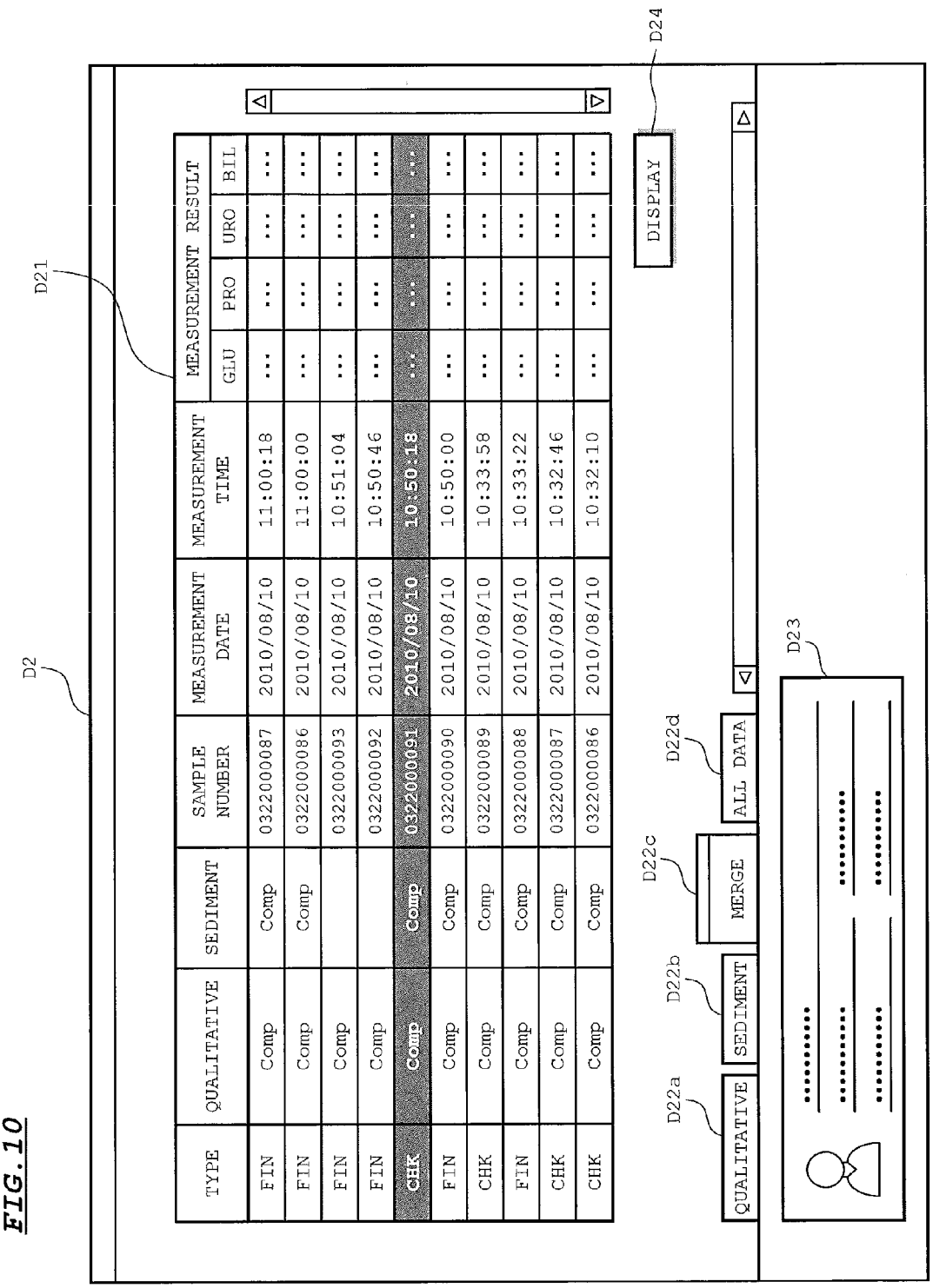
FIG. 10 shows a result displaying screen for displaying results of a measurement performed by a urine analyzer according to an embodiment.

FIG. 10 shows the result displaying screen D2 for displaying results of measurements performed by the urine analyzer 1. The result displaying screen D2 is displayed on the display section 420, in accordance with an instruction to display it made by the user.

The result displaying screen D2 includes a list displaying region D21, switching tabs D22a to D22d, a patient information displaying region D23, and a display button D24.

The list displaying region D21 is configured such that its display is switched in accordance with a switching tab selected from among the switching tabs D22a to D22d. FIG. 10 shows a state where merged data based on the merged DB is displayed with the switching tab D22c selected. In the list displaying region D21 in this state, a type item, a qualitative item, a sediment item, a sample number item, a measurement date item, a measurement time item, and a measurement result item for storing a plurality of results of the measurements are displayed.

In the type item, a character string of "FIN" or "CHK" is displayed. When "FIN" is displayed, it indicates that the merged data shown in this line includes no check item determined as an error (all 0s) in the cross-check result item. When "CHK" is displayed, it indicates that the merged data shown in this line includes a check item determined as an error in the cross-check result item.

In the qualitative item and the sediment item, information regarding the measurement performed by the urine qualitative measurement part 10 and information regarding the measurement performed by the urinary sediment measurement part 20 are displayed, respectively. When "Comp" is displayed in these items, it indicates that measurement results shown in the merged data of this line were normally obtained.

In the sample number item, the sample number based on which the merged data shown in this line was generated is displayed. In the measurement date item and the measurement time item, the measurement date item and measurement time item of the merged DB are displayed, respectively. The measurement result item includes all the qualitative measurement items and all the sediment measurement items, and results of the corresponding qualitative measurement and results of the corresponding sediment measurement are displayed.

When one of the switching tabs D22a to D22c is clicked, corresponding qualitative measurement results based on the qualitative measurement DB, sediment measurement results based on the sediment measurement DB, or merged data based on the merged DB are displayed in the list displaying region D21. When the switching tab D22d is clicked, all of the information displayed when each of the switching tabs D22a to D22c is clicked is displayed in the list displaying region D21.

In the patient information displaying region D23, patient information obtained based on the sample number of the line clicked in the list displaying region D21 is displayed. When a line in the list displaying region D21 is clicked while merged data is shown in the list displaying region D21 as shown in FIG. 10, and then the display button D24 is clicked while the line is displayed in the reversed manner as shown in FIG. 10, the detail of the merged data shown in this line is displayed in the merged data displaying screen D3.

Figure 11:
FIG. 11 shows a merged data displaying screen according to an embodiment.

FIG. 11 shows the merged data displaying screen D3. In the merged data displaying screen D3 shown in FIG. 11, the merged data of the fifth line from the top of the list displaying region D21 shown in FIG. 10 is displayed.

The merged data displaying screen D3 includes a sample information displaying region D31, a patient information displaying region D32, a qualitative measurement result displaying region D33, sediment measurement result displaying regions D34 and D35, and a cross-check result displaying region D36.

In the sample information displaying region D31, information of the sample which is the source of the measurement results displayed in the merged data displaying screen D3 is displayed. In the patient information displaying region D32, information of the patient from whom the sample was collected is displayed.

In the qualitative measurement result displaying region D33, a list of results of the qualitative measurement is displayed. In the sediment measurement result displaying region D34, a list of results of the sediment measurement is displayed. In the sediment measurement result displaying region D35, the results of the sediment measurement are displayed in scattergrams. In the cross-check result displaying region D36, results of the cross-checks performed regarding this merged data are displayed. When there is no cross-check that has been determined as an error, the cross-check result displaying region D36 remains blank.

Figure 12:
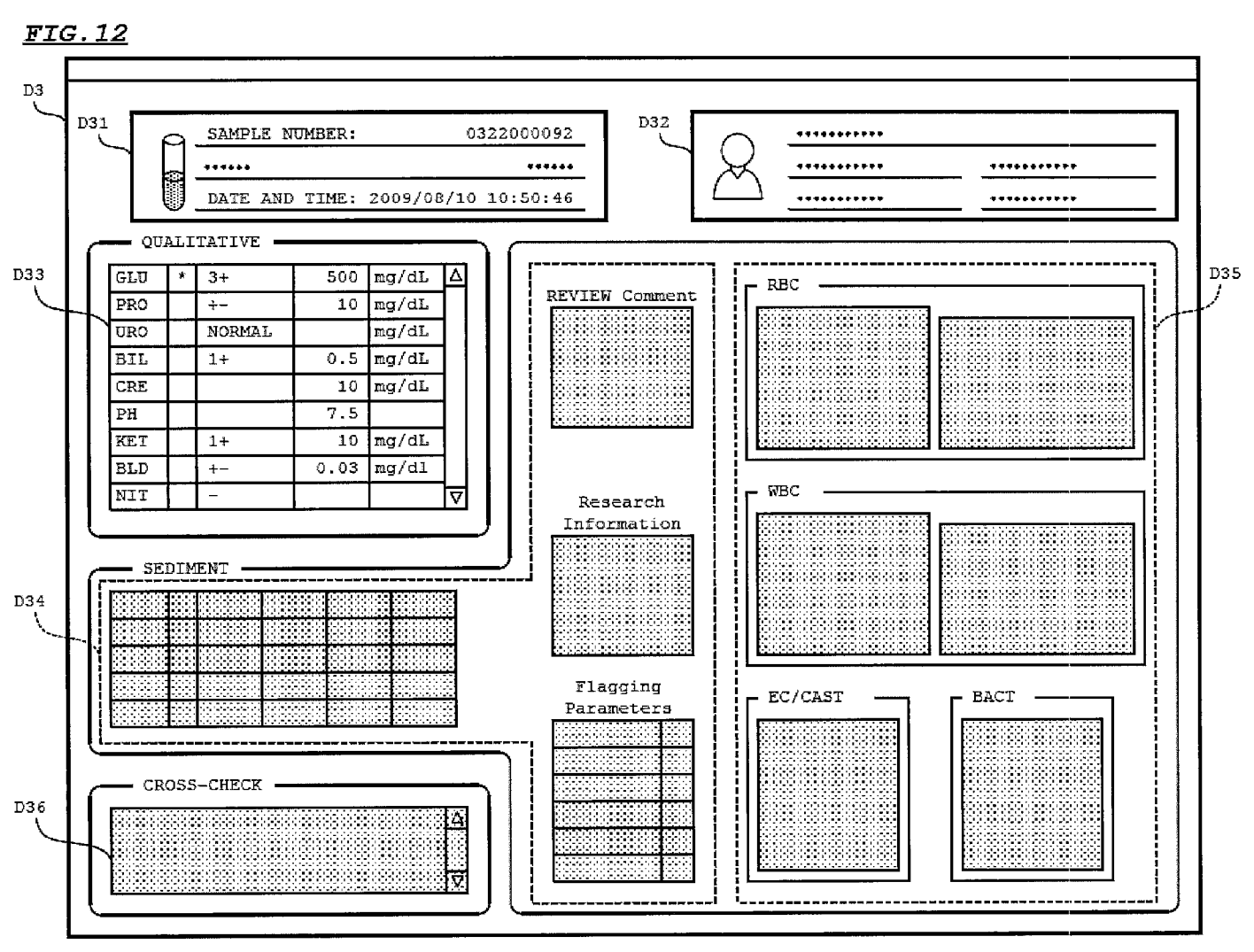

FIG. 12 shows the merged data displaying screen D3 when displaying merged data including only a qualitative measurement result. In the merged data displaying screen D3 shown in FIG. 12, merged data of the fourth line from the top of the list displaying region D21 shown in FIG. 10 is displayed.

Different from the merged data displaying screen D3 shown in FIG. 11, the merged data displaying screen D3 in this case does not include a sediment measurement result. Thus, the sediment measurement result displaying regions D34 and D35 are displayed in gray. In addition, the cross-check result displaying region D36 is also displayed in gray since no cross-check has been performed.

It should be noted that, when merged data including only a sediment measurement result is displayed, results of the sediment measurement are displayed in the sediment measurement result displaying regions D34 and D35, and the qualitative measurement result displaying region D33 and the cross-check result displaying region D36 are displayed in gray.

As described above, according to the present embodiment, when a qualitative measurement result is obtained, if a sediment measurement result that has the same sample number and that had been obtained within a set time period has been stored in the sediment measurement DB, a cross-check is performed based on these measurement results. Further, when a sediment measurement result is obtained, if a qualitative measurement result that has the same sample number and that had been obtained within the set time period has been stored in the qualitative measurement DB, a cross-check is performed based on these measurement results. Therefore, irrespective of which of a measurement by the urine qualitative measurement part 10 and a measurement by the urinary sediment measurement part 20 is performed first, a cross-check can be performed. This can reduce burden on the user, and thus allow smooth comparison and evaluation of measurement results.

Further, when a qualitative measurement result is obtained, if its corresponding sediment measurement result stored in the sediment measurement DB had been obtained within the set time period, the qualitative measurement result and the sediment measurement result are combined together, and a cross-check is performed. Further, when a sediment measurement result is obtained, if its corresponding qualitative measurement result stored in the qualitative measurement DB had been obtained within the set time period, the sediment measurement result and the qualitative measurement result are combined together, and a cross-check is performed. This prevents a cross-check from being performed based on a result of a measurement performed on a sample deteriorated due to lapse of time. Accordingly, a high accuracy of a cross-check can be maintained.

Further, according to the present embodiment, when a qualitative measurement result is obtained, if a sediment measurement result that has the same sample number and that had been obtained within the set time period has been stored in the sediment measurement DB, the number in the number item of the qualitative measurement DB and the number in the number item of the sediment measurement DB (combination information) for combining the qualitative measurement result and the sediment measurement result are stored in the merged DB. In addition, a cross-check is performed based on these measurement results, and its cross-check result is stored in the merged DB. Similarly, when a sediment measurement result is obtained, if a qualitative measurement result that has the same sample number and that had been obtained within the set time period has been stored in the qualitative measurement DB, the number in the number item of the qualitative measurement DB and the number in the number item of the sediment measurement DB (combination information) for combining the qualitative measurement result and the sediment measurement result are stored in the merged DB. In addition, a cross-check is performed based on these measurement results, and its cross-check result is stored in the merged DB. Furthermore, such combination information and cross-check results are added to the merged DB with some past information thereof retained. Accordingly, with respect to the same sample, the user can compare combinations of a qualitative measurement result and a sediment measurement result with each other, and thus, can more appropriately evaluate the measurement results of the sample.

Further, when a qualitative measurement result is obtained, if its corresponding sediment measurement result stored in the sediment measurement DB had not been obtained within the set time period, no combination information and no cross-check result are stored in the merged DB. Similarly, when a sediment measurement result is obtained, if its corresponding qualitative measurement result stored in the qualitative measurement DB had not been obtained within the set time period, no combination information and no cross-check result are stored in the merged DB. Accordingly, combination information and a cross-check result that are based on results of measurements performed on a sample deteriorated due to lapse of time will not be stored in the merged DB. This makes it possible to more appropriately evaluate the measurement results of the sample.

Further, according to the present embodiment, the user can select a record in the merged DB via the result displaying screen D2 shown in FIG. 10, and can cause the display section 420 to display the merged data displaying screen D3 displaying a combination of measurement results and a corresponding cross-check result, as shown in FIG. 11 or FIG. 12. Accordingly, with respect to the same sample, the user can compare its qualitative measurement result and its sediment measurement result in combination, and thus, can more appropriately evaluate the measurement results.

Further, simply by selecting a desired record on the result displaying screen D2 shown in FIG. 10 and operating the display button D24 thereon, the user can cause the combination of the measurement results and the cross-check result of the desired record to be displayed. Accordingly, for example, even when a plurality of measurements have been performed on the same sample, the user can cause each measurement result to be displayed through simple operations and compare them.

Further, in the merged data displaying screen D3, along with a qualitative measurement result and a sediment measurement result, scattergrams based on the sediment measurement result are displayed as shown in the sediment measurement result displaying region D35. Accordingly, with respect to the same sample, the user can compare the combination of the measurement results together with the scattergrams of the sediment measurement. Thus, the user can more appropriately evaluate the measurement results of the sample.

Further, according to the present embodiment, when a urine qualitative measurement is not necessary, if one or more sediment measurement results have been stored in the sediment measurement DB, a link only to the latest sediment measurement result is stored in the merged DB. When a urinary sediment measurement is not necessary, if one or more qualitative measurement results have been stored in the qualitative measurement DB, a link only to the latest qualitative measurement result is stored in the merged DB. Accordingly, even when only one of a qualitative measurement and a sediment measurement is performed, its measurement result is stored in the merged DB. Thus, a measurement result that does not have a target to be combined together, i.e., that includes either one of a qualitative measurement result and a sediment measurement result, can also be displayed as appropriate through similar processes to those in the case of a measurement result that has a target to be combined together. Therefore, by referring to the result displaying screen D2 shown in FIG. 10, the user can confirm that such a measurement result does not have a target to be combined together for a cross-check, and thus, can perform such confirmation operation simply and appropriately.

An embodiment of the present invention has been described. However, the embodiment of the present invention is not limited thereto.

For example, in the above embodiment, whether a measurement by the urine qualitative measurement part 10 is performed and whether a measurement by the urinary sediment measurement part 20 is performed are determined based on a qualitative measurement order and a sediment measurement order that are transmitted by the host computer 60, respectively. However, the present invention is not limited thereto. The user may determine whether a measurement by the urine qualitative measurement part 10 is performed and whether a measurement by the urinary sediment measurement part 20 is performed.

In this case, via the input section 410 (see FIG. 3) of the information processing apparatus 40, the user sets the information processing apparatus 40 such that it allows a measurement to be performed without making an inquiry about an order with the host computer 60. At this time, the user also sets which of urine qualitative measurement and urinary sediment measurement is performed, and on which items the measurement is performed. This setting is applied not on the basis of a sample but on the basis of a sample rack 50. Accordingly, on the basis of a sample rack 50, only one of the urine qualitative measurement and the urinary sediment measurement will be performed. After making such a setting, when the user sets a sample rack 50 holding sample containers 51 in the right vessel region 31a and starts the measurement, only one of the urine qualitative measurement and the urinary sediment measurement is performed on the samples.

Further, the user may cause only a urinary sediment measurement to be performed, by setting the information processing apparatus 40 such that it allows a manual measurement to be performed in the urinary sediment measurement part 20. In this case, the user sets a sample container 51 at a setting position for a manual measurement provided in a front portion of the urinary sediment measurement part 20. When a manual measurement is started, the nozzle of the urinary sediment measurement part 20 is moved to the setting position, and the sample is aspirated at this position. This makes it possible to preferentially perform a measurement by the urinary sediment measurement part 20 ahead of the other samples on the transport path 31.

As described above, in the urine analyzer 1, a measurement only by one of the urine qualitative measurement part 10 and the urinary sediment measurement part 20 can be performed. Accordingly, the user can cause a urine qualitative measurement or a urinary sediment measurement to be performed as appropriate. That is, after a sample is measured by the urinary sediment measurement part 20, the sample may be measured by the urine qualitative measurement part 10. Further, as described in the above embodiment, after a measurement by the urine qualitative measurement part 10 and a measurement by the urinary sediment measurement part 20 are sequentially performed, another measurement by the urine qualitative measurement part 10 or the urinary sediment measurement part 20 can be performed. Also in such a case, as in the above embodiment, a qualitative measurement result and a sediment measurement result may be stored in the qualitative measurement DB and the sediment measurement DB, respectively, and the merging processes shown in FIGS. 6 and 7 may be performed. In this case, S101 in FIG. 6 and S201 in FIG. 7 are omitted, and prior to the processing of the sample, the determinations in S102 in FIG. 6 and S202 and FIG. 7 are performed in accordance with the setting made by the user to the information processing apparatus 40. In the case of a manual measurement, since a urinary sediment measurement is always performed, the determination in S202 in FIG. 7 is always YES. Therefore, in the case of the manual measurement, the processes of S203 and thereafter are performed.

Further, in the above embodiment, a subject to be measured is exemplified by urine, but a subject to be measured may be blood. That is, the present invention can also be applied to a sample analyzer which tests blood, and further, the present invention can be applied to a clinical sample analyzer which tests other clinical samples.

Figure 13:
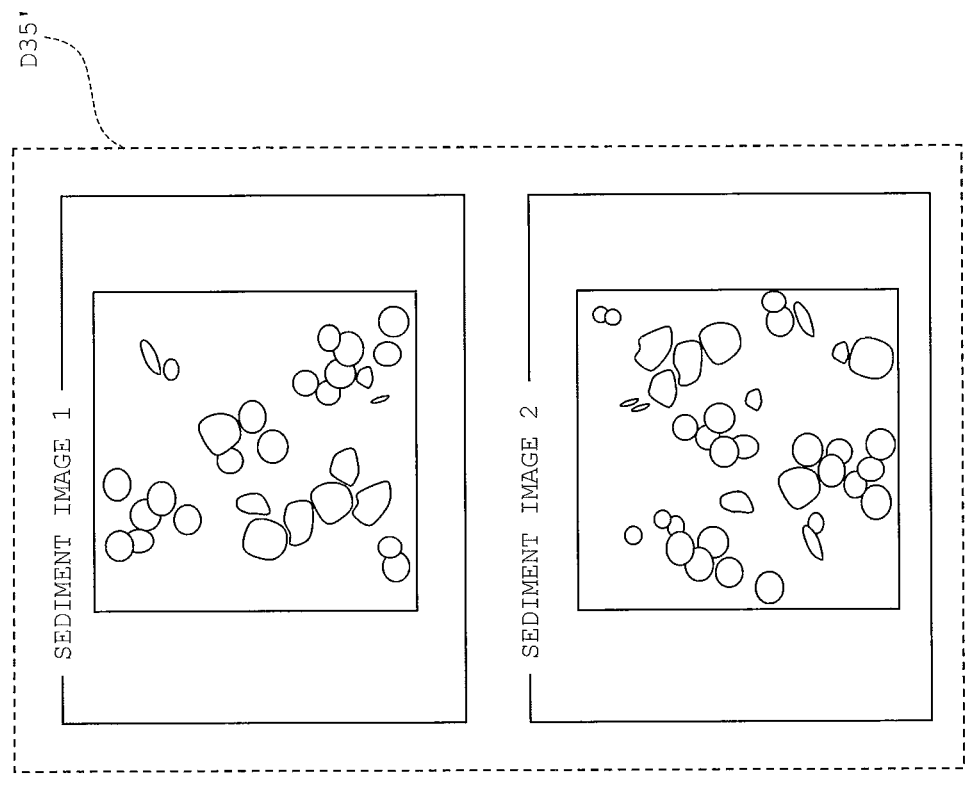
FIG. 13 shows a modified example of a sediment measurement result displaying region of a merged data displaying screen according to an embodiment.

Further, in the above embodiment, the measurement by the urinary sediment measurement part 20 is performed by using a flow cytometer. However, the present invention is not limited thereto. The measurement by the urinary sediment measurement part 20 may be performed by an image of a urine sample being taken and the taken sediment image being analyzed. In this case, instead of the scattergrams displayed in the sediment measurement result displaying region D35 shown in FIGS. 11 and 12, a sediment measurement result displaying region D35' (see FIG. 13) including such taken sediment images may be displayed. Further, the sediment measurement result displaying region D35' may be displayed along with the scattergrams displayed in the sediment measurement result displaying region D35 in FIGS. 11 and 12. When the sediment measurement result displaying region D35' is displayed in this manner, the user can compare, with respect to the same sample, a combination of measurement results together with the sediment images, and thus, can more appropriately evaluate the measurement results of the sample.

Further, in the above embodiment, in the merged DB, the number in the number item of the qualitative measurement DB and the number in the number item of the sediment measurement DB are stored. However, the present invention is not limited thereto. A qualitative measurement result and a sediment measurement result that are combined together may be directly stored in the merged DB. Further, in the merged DB, information of, for example, the dates and times of a qualitative measurement and the date and time of a sediment measurement to be combined together, may be stored. The information stored in the merged DB in this manner also serves as "combination information". That is, "combination information" described in claims may be any information as long as it can extract a qualitative measurement result and a sediment measurement result combined together. It should be noted that, in the case as mentioned above where the measurement results or the dates and times of a qualitative measurement and a sediment measurement are stored instead of the number items of the qualitative measurement DB and the sediment measurement DB shown in FIG. 5A, the combination of such measurement results and the combination of such dates and times of the measurements do not provide identification of the sample based on which the combination is made. Therefore, in such a case, it is necessary to include the sample number in each record of the merged DB.

Further, in the above embodiment, when a qualitative measurement result is obtained, if its corresponding sediment measurement result stored in the sediment measurement DB had not been obtained within the set time period, combination information will not be stored in the merged DB. When a sediment measurement result is obtained, if its corresponding qualitative measurement result stored in the qualitative measurement DB had not been obtained within the set time period, combination information will not be stored in the merged DB. However, alternatively, when a qualitative measurement result is obtained, if its corresponding one or more sediment measurement results have been stored in the sediment measurement DB, irrespective of the time when the sediment measurement result(s) was obtained, combination information may be generated based on the obtained qualitative measurement result and the latest sediment measurement result stored in the sediment measurement DB, and the generated combination information may be stored in the merged DB. Similarly, when a sediment measurement result is obtained, if its corresponding one or more qualitative measurement results have been stored in the qualitative measurement DB, irrespective of the time when the qualitative measurement result(s) was obtained, combination information may be generated based on the obtained sediment measurement result and the latest qualitative measurement result stored in the qualitative measurement DB, and the generated combination information may be stored in the merged DB.

Further, in the above embodiment, when the CPU 401 receives a sediment measurement result, the CPU 401 determines whether there is a qualitative measurement result that had been obtained within the set time period before the time at which the sediment measurement result was received, and if there is such a qualitative measurement result, a cross-check of the sediment measurement result and the qualitative measurement result is performed. However, the present invention is not limited thereto. For example, in the case where the CPU 401 receives a sediment measurement result, the CPU 401 may determine whether there is a qualitative measurement result that had been obtained within the set time period before the time at which the sediment measurement ended, and if there is such a qualitative measurement result, the CPU 401 may combine the sediment measurement result and the qualitative measurement result together to perform a cross-check, or alternatively, the CPU 401 may determine whether there is a qualitative measurement result that had been obtained within the set time period before the time at which the sediment measurement result was transmitted from the urinary sediment measurement part 20. This applies mutatis mutandis to the case where the CPU 401 receives a qualitative measurement result and performs a cross-check of the qualitative measurement result and a sediment measurement result.

In addition to the above, various modifications can be made as appropriate to the embodiment of the present invention without departing from the scope of the technical idea defined by the claims.

What is claimed is:

1. A urine analyzer comprising:
a qualitative measurement part comprising a first aspiration device that aspirates a first portion of a sample from a sample container and a detection section configured to perform measurement for a urine qualitative measurement item in the first portion;
a sediment measurement part comprising a second aspiration device that aspirates a second portion of the sample from the sample container and a detection section configured to perform measurement for a urinary sediment measurement item in the second portion;
a storage section for storing a qualitative measurement result obtained by the qualitative measurement part and a sediment measurement result obtained by the sediment measurement part; and
a controller configured to perform, when the qualitative measurement result of the sample is obtained and the sediment measurement result of the sample has been stored in the storage section, a cross-check of the obtained qualitative measurement result and the stored sediment measurement result, and to perform, when the sediment measurement result of the sample is obtained and the qualitative measurement result of the sample has been stored in the storage section, a cross-check of the obtained sediment measurement result and the stored qualitative measurement result, wherein
the controller performs the cross-check of the obtained qualitative measurement result and the stored sediment measurement result, if the qualitative measurement result is obtained within a predetermined time period after the stored sediment measurement result of the sample was obtained, and
the controller performs the cross-check of the obtained sediment measurement result and the stored qualitative measurement result, if the sediment measurement result is obtained within a predetermined time period after the stored qualitative measurement result of the sample was obtained.

2. The urine analyzer according to claim 1, further comprising a setting section configured to receive a setting of the predetermined time period.

3. The urine analyzer according to claim 2, wherein the storage section further stores the predetermined time period, and a default value of the time period is set to be longer than or equal to 15 minutes and shorter than or equal to 60 minutes.

4. The urine analyzer according to claim 1, wherein
the controller performs the cross-check of the obtained qualitative measurement result and the stored sediment measurement result, if the controller receives the qualitative measurement result from the qualitative measurement part within the predetermined time period after the stored sediment measurement result of the sample was obtained, and
the controller performs the cross-check of the obtained sediment measurement result and the stored qualitative measurement result, if the controller receives the sediment measurement result from the sediment measurement part within the predetermined time period after the stored qualitative measurement result of the sample was obtained.

5. The urine analyzer according to claim 1, wherein
the storage section stores a first database regarding qualitative measurement results, a second database regarding sediment measurement results, and a third database regarding combinations of a qualitative measurement result and a sediment measurement result,
if the sediment measurement result of the sample has been stored in the second database at the time when the qualitative measurement result is obtained, the controller stores, in the third database, combination information indicating a combination of the obtained qualitative measurement result and the stored sediment measurement result, and
if the qualitative measurement result of the sample has been stored in the first database at the time when the sediment measurement result is obtained, the controller stores, in the third database, combination information indicating a combination of the obtained sediment measurement result and the stored qualitative measurement result.

6. The urine analyzer according to claim 5, wherein the controller further stores, in the third database, a result of a cross-check of the combination of the qualitative measurement result and the sediment measurement result.

7. The urine analyzer according to claim 1, further comprising a transport part configured to transport the sample from the qualitative measurement part to the sediment measurement part.

8. A urine sample information processing method comprising:
aspirating a first portion of a sample from a sample container and measuring the first portion for a urine qualitative measurement item;
aspirating a second portion of the sample from the sample container and measuring the second portion for a urinary sediment measurement item;
storing, in a storage section, the qualitative measurement result obtained by measuring the first portion for the urine qualitative measurement item;
storing, in the storage section, a sediment measurement result obtained by measuring the second portion for a urinary sediment measurement item;
performing, if the sediment measurement result of the sample has been stored in the storage section at the time when the qualitative measurement result of the sample is obtained, a cross-check of the qualitative measurement result and the sediment measurement result if the qualitative measurement result is obtained within a predetermined time period after the stored sediment measurement result of the sample was obtained; and
performing, if the qualitative measurement result of the sample has been stored in the storage section at the time when the sediment measurement result of the sample is obtained, a cross-check of the sediment measurement result and the qualitative measurement result if the sediment measurement result is obtained within a predetermined time period after the stored qualitative measurement result of the sample was obtained.

9. A urine analyzer comprising:
a qualitative measurement part comprising a first aspiration device that aspirates a first portion of a sample from a sample container and a detection section configured to perform a measurement for a urine qualitative measurement item in the first portion;
a sediment measurement part comprising a second aspiration device that aspirates a second portion of the sample from the sample container and a detection section configured to perform a measurement for a urinary sediment measurement item in the second portion;
a storage section configured to store the qualitative measurement result obtained by the qualitative measurement part, the sediment measurement result obtained by the sediment measurement part, and combination information indicating a combination of the qualitative measurement result and the sediment measurement result; and
a controller, wherein
the controller combines the qualitative measurement result newly obtained with a latest sediment measurement result among one or more sediment measurement results of the sample, the one or more sediment measurement results including a sediment measurement result already combined with other qualitative measurement result, and
the controller combines the sediment measurement result newly obtained with a latest qualitative measurement result among one or more qualitative measurement results of the sample, the one or more qualitative measurement results including a qualitative measurement result already combined with other sediment measurement result.

10. The urine analyzer according to claim 9, wherein
the controller combines the qualitative measurement result with the latest sediment measurement result among one or more sediment measurement results of the sample that had been obtained within a predetermined time period, and
the controller combines the sediment measurement result with the latest qualitative measurement result among one or more qualitative measurement results of the sample that had been obtained within the predetermined time period.

11. The urine analyzer according to claim 10, wherein
the controller combines the qualitative measurement result with the latest sediment measurement result among one or more sediment measurement results of the sample that had been obtained within the predetermined time period before a time at which the qualitative measurement result was obtained, and
the controller combines the sediment measurement result with the latest qualitative measurement result among one or more qualitative measurement results of the sample that had been obtained within the predetermined time period before a time at which the sediment measurement result was obtained.

12. The urine analyzer according to claim 9, further comprising:
a display, wherein
in a case where the storage section stores first combination information regarding a first combination and second combination information regarding a second combination, the first and second combinations having common one of the qualitative or sediment measurement result, the controller is operable to cause the display to display a first screen which includes the commonly included measurement result and other measurement result according to a first combination, and a second screen which includes the commonly included measurement result and other measurement result according to a second combination.

13. The urine analyzer according to claim 12, wherein the controller is operable to cause the display to display a reception screen for receiving a selection from the first and second combinations.

14. The urine analyzer according to claim 9, further comprising a display,
wherein the controller causes the display to display, along with the qualitative measurement result and the sediment measurement result combined together in accordance with combination information stored in the storage section, a scattergram based on the sediment measurement result or a sediment image taken in a corresponding sediment measurement.

15. The urine analyzer according to claim 9, wherein the controller performs a cross-check of the qualitative measurement result and the sediment measurement result combined together in accordance with combination information, and stores a result of the cross-check in the storage section.

16. The urine analyzer according to claim 15, further comprising a display, wherein the controller causes the display section to display the result of the cross-check stored in the storage section, and the qualitative measurement result and the sediment measurement result corresponding to the cross-check.

17. The urine analyzer according to claim 16, wherein the controller causes the display to display a measurement result screen including the result of the cross-check, and the qualitative measurement result and the sediment measurement result corresponding to the cross-check.

18. The urine analyzer according to claim 9, further comprising a communication section which receives a measurement order,
wherein when the controller receives, via the communication section, information indicating that the qualitative measurement is not necessary to be performed on the sample, if the sediment measurement result of the sample has been stored in the storage section, the controller stores, in the storage section, combination information including only the stored sediment measurement result, and when the controller receives, via the communication section, information indicating that the sediment measurement is not necessary to be performed on the sample, if the qualitative measurement result of the sample has been stored in the storage section, the controller stores, in the storage section, combination information including only the stored qualitative measurement result.

19. A urine sample information processing method comprising:

aspirating a first portion of a sample from a sample container and measuring the first portion for a urine qualitative measurement item;
aspirating a second portion of the sample from the sample container and measuring the second portion for a urinary sediment measurement item;
storing, in a storage section, a qualitative measurement result obtained by measuring the first portion for the urine qualitative measurement item;
storing, in the storage section, a sediment measurement result obtained by measuring the second portion for the urinary sediment measurement item;
combining the qualitative measurement result newly obtained with a latest sediment measurement result among one or more sediment measurement results of the sample, the one or more sediment measurement results including a sediment measurement result already combined with other qualitative measurement result; and
combining the sediment measurement result newly obtained with a latest qualitative measurement result among one or more qualitative measurement results of the sample, the one or more qualitative measurement results including a qualitative measurement result already combined with other sediment measurement result.

* * * * *